USOO5614617A

United States Patent [19]
Cook et al.

[11] Patent Number: 5,614,617
[45] Date of Patent: Mar. 25, 1997

[54] NUCLEASE RESISTANT, PYRIMIDINE MODIFIED OLIGONUCLEOTIDES THAT DETECT AND MODULATE GENE EXPRESSION

[75] Inventors: Philip D. Cook, Carlsbad; Yogesh S. Sanghvi, San Marcos, both of Calif.

[73] Assignee: Isis Pharmaceuticals, Inc., Carlsbad, Calif.

[21] Appl. No.: 971,978

[22] PCT Filed: Jul. 1, 1991

[86] PCT No.: PCT/US91/04681

§ 371 Date: Feb. 18, 1993

§ 102(e) Date: Feb. 18, 1993

[87] PCT Pub. No.: WO92/02258

PCT Pub. Date: Feb. 20, 1992

[51] Int. Cl.$^6$ .................. C07H 21/02; C07H 21/04; C07H 19/10; A61K 31/70
[52] U.S. Cl. .................. 536/23.1; 536/24.3; 536/24.31; 536/24.32; 536/24.33; 536/24.5; 536/28.1; 536/28.3; 536/28.54; 435/6; 436/94
[58] Field of Search .................. 514/44, 49; 536/23.1, 536/24.3, 24.31, 24.32, 24.5, 26.8, 24.33, 28.1, 28.3, 28.54, 28.55; 435/6; 935/3, 6–8, 33–35, 38, 44–46

[56] References Cited

U.S. PATENT DOCUMENTS

| | | | |
|---|---|---|---|
| 3,235,363 | 2/1966 | Luckenbauth et al. | 71/2.5 |
| 4,458,066 | 7/1984 | Caruthers et al. | 536/27 |
| 4,711,955 | 12/1987 | Ward et al. | 536/29 |
| 4,948,882 | 8/1990 | Ruth | 536/27 |
| 4,965,350 | 10/1990 | Inoue et al. | 536/28 |

FOREIGN PATENT DOCUMENTS

WO86/05518  9/1986  WIPO.

OTHER PUBLICATIONS

Lisziewicz et al. Antisense Oligodeoxynucleotide phosphorothioate complementary to Gag mRNA blocks replication of human immunodeficiency virus type 1 in human peripheral blood cells *Proc. Natl. Acad. Sci.* 1994 91:7942.
Ramazeilles et al. Antisense phophorothioate oligonucleotids: Selective killing of the intracellular parasite *Leishmania amazonensis Proc. Natl. Acad. Sci.* 1994 91:7959.
Soreq et al. Antisense ologinucleotide inhibition of acetylcholinesterase gene expression induces progenitor cell expansion and suppresses hemtopoietic apoptosis ex vivo *Proc. Natl. Acad. Sci.* 1994 91:7907.
Sanghvi et al. Synthesis and Biological Evaluation of Antisense Oligonucleotides Containing Modified Pyrimidines, *Nucleosides and Nucleotides* 1991 10:345–346.
Lehninger A.L. Biochemistry, 2nd. Ed., Worth Publishers, Inc. New York 1975 321–322.
Metzler, D.E., *Biochemistry*, N.Y., Academic Press, 1977, pp. 873–878, QH611. M596c.
E. Uhlmann et al., "Antisense Oligonucleotides: A New Therapeutic Principle", Chemical Reviews, vol. 90, #4 (Jun. 1990) pp. 543–584.

B. Tseng et al., "Antisense Oligonucleotide Technology & Cancer Therapy" Cancer Gene Therapy, vol. 1 #1 (Mar. 1994) pp. 65–71.
C. Stein et al., "Antisense Oligonucleotide as Therapeutic Agents" Science, vol. 261 (Aug. 20, 1993) pp. 1004–1012.
C. Mirabelli et al., "Activities of Antisense Oligonucleotides" Anti–Cancer Drug Design, vol. 6 (Dec. 1991) pp. 647–661.
W.S. Zielinski et al. "Chemical Synthesis of 5–azacy–idine Nucleotides" Nucleic Acids Research vol. 12, #12 (1984) pp. 5025–5036.
V. Lisy et al. "Oligonucleotides containing G–Aza pyrimidine Ribonucleosides" Collection Czechoslav. Chem. Commun., vol. 33 (1968) pp. 4111–4119.
R. Weiss, "Upping the Antisense Ante" Science News, vol. 139 (Feb. 16, 1991) pp. 108–109.
J. Cohen, "Oligonucleotides as Therapeutic Agents", Pharmac. Therap. vol. 52 (1991) pp. 211–225.
S. Shibahara et al., "Size–Directed Cleavage of RNA", Nucl. Ac. Res., vol. 15 #11 (1987) pp. 4403–4415.
Cohen, *Oligonucleotides: Antisense Inhibitors of Gene Expression*, Boca Raton, FL: CRC Press, Inc., 1989.
Crisp et al., "Synthesis of 5–Aryluridines and 5–Aryl–2'–deoxyuridines," *Synthetic Communications*, 20:413–422, 1990.
Cristescu, C. "AS–Triazine Derivatives with Potential Therapeutic Action. XIV," *Rev. Roumaine Chim.*, 20:1287–1273, 1975.
Fox et al., "Thiation of Nucleosides. II. Synthesis of 5–Methyl–2'–deoxycytidine and Related Pyrimidine Nucleosides," *J. Amer. Chem. Society*, 81:178–187, 1959.
Freskos, J., "Synthesis of 2'–Deoxypyrimidine Nucleosides via copper (I) iodide catalysis,", *Nucleosides & Nucleotides*, 8:1075–1076, 1989.
Habener et al., "5–Fluorodeoxyuridine as an alternative to the synthesis of mixed hybridization probes for the detection of specific gene sequences," *Proc. Natl. Acad.*
Hayakawa et al., "A Simple and General Entry to 5–Substituted Uridines Based on the Regioselective Lithiation Controlled by A Protecting Group in the Sugar Moeity," *Tetrahedron Letters*, 28:87–90, 1987.
Miller et al., "A new approach to chemotherapy based on molecular biology and nucleic acid chemistry: Matagen (masking tape for gene expression)," *Anti–Cancer Drug Design*, 2:117–128, 1987.
Su et al., "Nucleosides. 127. Synthesis of Pyrido[2,3–d] pyrimidine nucleosides from 5–cyanouridine,", *Nucleosides and Nucleotides*, 3:513–524, 1984.
Wang et al., "A Novel Cyclization Reaction of a C–6 Substituted Uridine Analog: An Entry to 5,6–Dialkylated Uridine Derivatives," *Tetrahedron Letters*, 30:7005–7008, 1989.

Primary Examiner—Charles Rories
Attorney, Agent, or Firm—Woodcock Washburn Kurtz Mackiewicz & Norris

[57] ABSTRACT

Oligonucleotide analogs are provided having improved nuclease resistance. Modifications of selected nucleotides through substitutions on the pyrimidine ring are disclosed. Certain preferred embodiments comprise the inclusion of said modified nucleotides at a plurality of sites, especially at the 3' end of a selected oligonucleotide analog.

18 Claims, No Drawings

NUCLEASE RESISTANT, PYRIMIDINE MODIFIED OLIGONUCLEOTIDES THAT DETECT AND MODULATE GENE EXPRESSION

CROSS REFERENCES TO RELATED APPLICATIONS

This application is a national stage filing under 35 U.S.C. 371 of International Application Ser. No. PCT/US91/04681 filed 1 Jul. 1991, which claims the benefit of U.S. Application Ser. No. 07/558,806 filed 27 Jul. 1990, now abandoned.

FIELD OF THE INVENTION

This invention relates to the design, synthesis and application of nuclease resistant oligonucleotides that are useful for antisense oligonucleotide therapeutics, diagnostics, and research reagents. Pyrimidine modified oligonucleotides that are resistant to nuclease degradation and are capable of modulating the activity of DNA and RNA are provided. Methods for modulating the production of proteins utilizing the modified oligonucleotides of the invention are also provided.

BACKGROUND OF THE INVENTION

It is well known that most of the bodily states in mammals including infectious disease states, are effected by proteins. Such proteins, either acting directly or through their enzymatic functions, contribute in major proportion to many diseases in animals and man.

Classical therapeutics has generally focused upon interactions with such proteins in efforts to moderate their disease causing or disease potentiating functions. Recently, however, attempts have been made to moderate the actual production of such proteins by interactions with molecules that direct their synthesis, intracellular RNA. By interfering with the production of proteins, it has been hoped to effect therapeutic results with maximum effect and minimal side effects. One approach for inhibiting specific gene expression is the use of oligonucleotides and oligonucleotide analogs as antisense agents.

Antisense methodology is the complementary hybridization of relatively short oligonucleotides to single-stranded mRNA or single-stranded DNA such that the normal, essential functions of these intracellular nucleic acids are disrupted. Hybridization is the sequence specific hydrogen bonding of oligonucleotides to Watson-Crick base pairs of RNA or single stranded DNA. Such base pairs are said to be complementary to one another.

Naturally occurring event that lead to disruption of the nucleic acid functions are discussed by Cohen in *Oligonucleotides: Antisense Inhibitors of Gene Expression*, (CRC Press, Inc., Boca Raton Fla., 1989). These authors proposes two possible types of terminating events. The first, hybridization arrest, denotes a terminating event in which the oligonucleotide inhibitor binds to the target nucleic acid and thus prevents, by simple steric hindrance, the binding of essential proteins, most often ribosomes, to the nucleic acid. Methyl phosphonate oligonucleotides; P. S. Miller & P.O.P. Ts'O, *Anti-Cancer Drug Design*," Vol. 2, pp. 117–128 (1987); and α-anomer oligonucleotides, Cohen J. S. ed., *Oligonucleotides: Antisense Inhibitors of Gene Expression*, (CRC Press, Inc., Boca Raton Fla. 1989), are two of the most extensively studied antisense agents that are thought to disrupt nucleic acid function by hybridization arrest.

A second type of terminating event for antisense oligonucleotides involves enzymatic cleavage of the targeted RNA by intracellular RNase H. The oligonucleotide or oligonucleotide analog, which must be of the deoxyribo type, hybridizes with the targeted RNA and this duplex activates the RNase H enzyme to cleave the RNA strand, thus destroying the normal function of the RNA. Phosphorothioate oligonucleotides are a prominent example of an antisense agent that operates by this type of antisense terminating event.

Considerable research is being directed to the application of oligonucleotides and oligonucleotide analogs as antisense agents for therapeutic purposes. Applications of oligonucleotides as diagnostics, research reagents, and potential therapeutic agents require that the oligonucleotides or oligonucleotide analogs be synthesized in large quantities, be transported across cell membranes or taken up by cells, appropriately hybridize to targeted RNA or DNA, and subsequently terminate or disrupt nucleic acid function. These critical functions depend on the initial stability of oligonucleotides towards nuclease degradation.

A serious deficiency of naturally occurring oligonucleotides and existing oligonucleotide analogs for these purposes, particularly those for antisense therapeutics, is the enzymatic degradation of the administered oligonucleotide by a variety of ubiquitous nucleolytic enzymes, intracellularly and extracellularly located, hereinafter referred to as "nucleases". It is unlikely that unmodified oligonucleotides will e useful therapeutic agents because they are rapidly degraded by nucleases. Modification of oligonucleotides to render them resistant to nucleases is therefore greatly desired.

Modifications of oligonucleotides to enhance nuclease-resistance have heretofore generally taken place on the sugar-phosphate backbone, particularly on the phosphorus atom. Phosphorothioates, methyl phosphonates, phosphoramidates, and phosphotriesters (phosphate methylated DNA) have been reported to have various levels of resistance to nucleases. However, while the ability of an antisense oligonucleotide to bind to specific DNA or RNA with fidelity is fundamental to antisense methodology, modified phosphorus oligonucleotides, while providing various degrees of nuclease resistance, have generally suffered from inferior hybridization properties.

One reason for this inferior hybridization may be due to the prochiral nature of the phosphorus atom. The modifications on the internal phosphorus atoms of modified phosphorous oligonucleotides result in Rp and Sp stereoisomers. Since a practical synthesis of stereoregular oligonucleotides (all Rp or Sp phosphate linkages) is unknown, oligonucleotides with modified phosphorus atoms have $n^2$ isomers with n equal to the length or the number of the bases in the oligonucleotide. Furthermore, modifications on the phosphorus atom have unnatural bulk about the phosphodiester linkage that interferes with the conformation of the sugar-phosphate backbone and consequently the stability of the duplex. The effects of phosphorus atom modifications cause inferior hybridization to the targeted nucleic acids relative to the unmodified oligonucleotide hybridizing to the same target.

The relative ability of an oligonucleotide to bind to complementary nucleic acids may be compared by determining the melting temperature of a particular hybridization complex. The melting temperature ($T_m$), a characteristic physical property of double helixes, denotes the temperature in degrees centigrade at which 50% helical versus coil (unhybridized) forms are present. $T_m$ is measured by using the UV spectrum to determine the formation and breakdown (melting) of hybridization. Base stacking that occurs during hybridization, is accompanied by a reduction in UV absorption (hypochromicity). Consequently, a reduction in UV absorption indicates a higher $T_m$. The higher the $T_m$, the greater the strength of the binding of the strands. Non-Watson-Crick base pairing has a strong destabilizing effect on the $T_m$. Consequently, absolute fidelity of base pairing is likely necessary to have optimal binding of an antisense oligonucleotide to its targeted RNA.

Considerable reduction in the hybridization properties of methyl phosphonates and phosphorothioates has been reported: see Cohen, J. S., ed. *Oligonucleotides: Antisense Inhibitors of Gene Expression*, (CRC Press, Inc., Boca Raton Fla., 1989). Methyl phosphonates have a further disadvantage in that the duplex it forms with RNA does not activate degradation by RNase H as an terminating event, but instead acts by hybridization arrest that can be reversed due to a helical melting activity located on the ribosome. Phosphorothioates are highly resistent to most nucleases. However, phosphorothioates typically exhibit non-antisense modes of action, particularly the inhibition of various enzyme functions due to nonspecific binding. Enzyme inhibition by sequence-specific oligonucleotides undermines the very basis of antisense chemotherapy.

Therefore, oligonucleotides modified to exhibit resistance to nucleases, to activate the RNase H terminating event, and to hybridize with appropriate strength and fidelity to its targeted RNA (or DNA) are greatly desired for anti-sense oligonucleotide diagnostics, therapeutics and research.

OBJECTS OF THE INVENTION

It is a principal object of the invention to provide oligonucleotide analogs for use in antisense oligonucleotide diagnostics, research reagents, and therapeutics.

It is further an object of the invention to provide such oligonucleotide analogs that are effective in modulating the activity of a DNA or an RNA.

Another object of the invention is to provide such oligonucleotide analogs that are less likely to invoke undesired or toxic side reactions.

Yet another object of the invention is to provide research and diagnostic methods and materials for assaying bodily states in animals, especially diseased states.

A further object of the invention is to provide therapeutic and research methods and materials for the treatment of diseases through modulation of the activity of DNA and RNA.

These and other objects will become apparent to persons of ordinary skill in the art from a review of the present specification and attendant claims.

SUMMARY OF THE INVENTION

In accordance with the present invention, compositions that are resistant to nuclease degradation and that modulate the activity of DNA or RNA are provided. These compositions are comprised of oligonucleotides that incorporate modified pyrimidine bases therein, the targeting portions of which are specifically hybridizable with preselected nucleotide sequences of single stranded or double-stranded DNA and RNA. The pyrimidine modified oligonucleotides recognize and form double strands with single stranded DNA and RNA or triple strands with double stranded DNA and RNA.

The nuclease resistant oligonucleotides consist of a strand of nucleic acid bases linked together through linking groups. The target portion of the nuclease resistant oligonucleotides may range in length from about 5 to about 50 nucleic acid bases. However, in accordance with preferred embodiments of this invention, a target sequence 15 bases in length is believed to be optimal.

The pyrimidine modified oligonucleotides of the invention incorporate bases including pyrimidines such as thymine, uracil or cytosine, or purines such as guanine or adenine, or modifications thereof, arranged in a selected sequence. The sugar moieties of such bases may be either deoxyribose or ribose sugars. The groups linking the bases together may be the usual sugar phosphate nucleic acid backbone, but may also be modified as a phosphorothioate, alkylphosphonates such as methylphosphonate, phosphotriester, phosphoamidate or other backbone modifications useful to further enhance the pyrimidine modified oligonucleotide properties. For example, the phosphodiester linkage may also be replaced by a carbon or ether linkage.

In accordance with other preferred embodiments of this invention, the targeting portion may be an analog of an oligonucleotide wherein at least one Of the pyrimidine bases, thymine, cytosine, or uracil, have been substituted with a modified nucleic acid base, which is faithful to the Watson-Crick hydrogen-bonding base pair rules (T to A, C to G and U to A), yet confers nuclease resistance to the oligonucleotide. Modification of the pyrimidine base or bases preferably occurs at the 5 or 6 positions of the pyrimidine ring. In the alternative, one or more of the pyrimidine bases may be modified at both the 5 and 6 positions of the pyrimidine ring.

The substitutions that may occur at the 5 and 6 positions may include additions of hetero atoms for the carbon atoms at the 5 and 6 positions of the pyrimidine or the addition methyl, hydroxyl, ether, alcohol, benzyl, or phenyl groups. The modifications may also involve the addition of nitro groups, thiol groups, halogen groups or halocarbon groups including fluorocarbon groups. In the alternative, the modification may be a carbocyclic or heterocyclic ring that is formed via fusion of a substrate to the 5 and 6 positions of the pyrimidine ring. The additions that occur at the 5 and 6 positions may, but need not be, the same.

The resulting novel oligonucleotides are resistant to nuclease degradation and exhibit hybridization properties of higher quality relative to wild type (DNA-DNA and RNA-DNA) duplexes and the presently known phosphorus modified oligonucleotide antisense duplexes containing phosphorothioates, methylphosphonates, phosphoramidates and phosphotriesters. The invention is also directed to methods for modulating the production of a protein by an organism comprising contacting the organism with a composition formulated in accordance with the foregoing considerations. It is preferred that the RNA or DNA portion that is to be modulated be preselected to comprise that portion of DNA or RNA that codes for the protein whose formation is to be modulated. The targeting portion of the composition to be employed is, thus, selected to be complementary to the preselected portion of DNA or RNA, that is to be an antisense oligonucleotide for that portion.

This invention is also directed to methods for treating an organism having a disease characterized by the undesired production of a protein. This method comprises contacting the organism with a composition in accordance with the foregoing considerations. The composition is preferably one which is designed to specifically bind with messenger RNA that codes for the protein whose production is to be inhibited.

The invention further is directed to diagnostic methods for detecting the presence or absence of abnormal RNA molecules or abnormal or inappropriate expression of normal RNA molecules in organisms or cells.

This invention is also directed to methods for the selective binding of RNA for research and diagnostic purposes. Such selective, strong binding is accomplished by interacting such RNA or DNA with compositions of the invention that are resistance to degradative nucleases and that hybridize stronger and with greater fidelity than known oligonucleotides or oligonucleotide analogs.

DETAILED DESCRIPTION OF PREFERRED EMBODIMENTS

The compositions useful for modulating the activity of an RNA or DNA molecule in accordance with this invention generally comprise a modified pyrimidine containing oligonucleotide of a target sequence that is specifically hybridizable with a preselected nucleotide sequence of single stranded or double stranded DNA or RNA molecule and that is nuclease resistant.

It is generally desirable to select a sequence of DNA or RNA for or which is involved in the production of proteins whose synthesis is ultimately to be modulated or inhibited in entirety. The targeting portion of the composition is generally an oligonucleotide analog. It is synthesized, conveniently through solid state synthesis of known methodology, to be complementary to or at least to be specifically hybridizable with the preselected nucleotide sequence of the RNA or DNA. Nucleic acid synthesizers are commercially available and their use is generally understood by persons of ordinary skill in the art as being effective in generating nearly any oligonucleotide of reasonable length that may be desired.

In the context of this invention, the term "oligonucleotide" refers to a plurality of joined nucleotide units formed in a specific sequence from naturally occurring bases and pentofuranosyl sugar groups joined through an internucleotide linking group by native phosphodiester bonds. These nucleotide units may be nucleic acid bases such as guanine, adenine, cytosine, thymine or uracil. The sugar group may be a deoxyribose or ribose sugar. This term refers to both naturally occurring or synthetic species formed from naturally occurring subunits.

"Oligonucleotide analog" as the term is used in connection with this invention, refers to moieties that function similarly to oligonucleotides but which have non-naturally occurring portions. Oligonucleotide analogs may have altered sugar moieties or inter-sugar linkages, for example, phosphorothioates and other sulfur containing species which are known for use in the art. Oligonucleotide analogs may also comprise altered base units or other modifications consistent with the spirit of this invention, and in particular such modifications as may increase nuclease resistance of the oligonucleotide composition in order to facilitate antisense therapeutic, diagnostic or research reagent use of a particular oligonucleotide.

It is generally preferred for use in some embodiments of this invention that some positions of the nucleotide base be substituted in order to increase the nuclease resistance of the composition while maintaining the integrity of the oligonucleotide binding capabilities. Such substitutions may occur at the 5 or 6 position of one or more pyrimidine rings by substituting a heteroatom for a carbon atom of the pyrimidine ring at these positions. In the alternative, the nuclease resistance of the oligonucleotide may be increased by addition of a substituent group at the 5 and 6 positions of the pyrimidine ring.

Substituent groups may be methyl, hydroxyl, alkoxy, alcohol, ester, benzyl, phenyl, nitro, thiol, thioalkoxy, halogen, halocarbon or fused carbon rings or heteroatom containing rings. In accordance with some preferred embodiments of the invention, substitutions of the pyrimidine ring may be aza at the 5 or 6 or both the 5 and 6 position. In accordance with other preferred embodiments of the invention, substituent groups added to the 5 or 6 positions may be one or more of nitro-, methyl-, bromo-, iodo-, chloro-, fluoro-, trifluoro-, trifluoromethyl-, 2,4- dinitrophenyl-, mercapto-, or methylmercapto- groups. Other additions that may also be preferred for use against nuclease degradation are ethers, thioethers, alcohols and thioalcohols such as HS—C—, MeS—C—, OH—C—, MeO—C—, HOCH$_2$—C—, and cyclopentyl, cyclohexyl and imidazo rings fused to the pyrimidine ring via the 5 and 6 positions of the pyrimidine ring. Accordingly, some preferred embodiments of this invention may incorporate a modified pyrimidine base or bases having the structure:

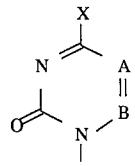

wherein X=OH or NH$_2$, and A and B may be the same or different and may be: C-lower alkyl, N, C—CF$_3$, C—F, C—Cl, C—Br, C—I, C-halocarbon including C-fluorocarbon, C—NO$_2$, C—OCF$_3$, C—SH, C—SCH$_3$, C—OH, C—O-lower alkyl, C—CH$_2$OH, C—CH$_2$SH, C—CH$_2$SCH$_3$, C—CH$_2$OCH$_3$, C—NH$_2$, C—CH$_2$NH$_2$, C-alkyl-NH$_2$, C-benzyl, C-aryl, C-substituted aryl, C-substituted benzyl; or one of A and B are as above and the other is C-H; or together A and B are part of a carbocyclic or heterocyclic ring fused to the pyrimidine ring through A and B. It is preferred that one or both of A and B be C-lower alkyl, C—O-lower alkyl, C—OH, C-phenyl, C-benzyl, C-nitro, C-thiol, C-halocarbon, or C-halogen. In accordance with other preferred embodiments, at least one of A and B is C-halogen or C-halocarbon including C-fluorocarbon, especially C-trifluoromethyl. Other fluorocarbon include C—C(CF$_3$)$_3$, C—CF$_2$—CF$_3$ and C—CF$_2$—CF$_2$—CF$_3$. Halogen includes fluorine, bromine, chlorine and iodine.

In accordance with other preferred embodiments, one or both of A and B are nitrogen atoms. It is still more preferred that A be nitrogen. In other embodiments, A is C—CH$_3$ or C—CF$_3$ and B is nitrogen or A is C—Br and B is nitrogen.

It is preferred that at least one modified pyrimidine be at one end of said oligonucleotide analog, especially at the 3' end of said oligonucleotide analog. In accordance with other, preferred embodiments, the oligonucleotide analogs contain up to about 3 modified pyrimidines incorporated at the 3' end of said oligonucleotide. In other embodiments, at least about 1% of said pyrimidines are modified. It is preferred in accordance with other embodiments to have greater quantities of modifications, such as at least about 10% of said pyrimidines, or even, 25%, 50% or substantially all of said pyrimidines.

The sugar moieties attached to the modified pyrimidine can be either a ribose or deoxyribose sugar. The sugar linking groups of the modified pyrimidine can be modified to a phosphorothioate, alkyl phosphonate including methyl phosphonate, phosphoamidate, phosphotriester or phosphate alkylate structure as well. In other embodiments, the oligonucleotide analogs can have sugar linking groups of the modified pyrimidines replaced with carbon or ether linkages.

For therapeutics, it is convenient that the oligonucleotide analog be prepared in a pharmaceutically acceptable carrier.

It is preferred in some embodiments of the present invention to employ pyrimidine modified oligonucleotides that are further modified. In this context, pyrimidine modified oligonucleotide analogs refers to structures that are generally similar to native oligonucleotides, but which have been modified in one or more significant ways.

Such modifications may take place at the sugar backbone of the invention. It is generally preferred to enhance the ability of the target sequence of the pyrimidine modified oligonucleotides to penetrate into the intracellular spaces of cells where the messenger RNA and the DNA, which are the targets of the overall composition, reside. Therefore, it is generally preferred to provide modifications of oligo nucleotides that are substantially less ionic than native forms in order to facilitate penetration of the oligonucleotide into the intracellular spaces. Any of the existing or yet to be discovered methods for accomplishing this goal may be employed in accordance with the practice of the present invention. At present, it has been found preferable to employ substitutions for the phosphodiester bond, which substitutions are not only relatively less ionic than the naturally occurring bonds but are also substantially non-chiral. As will be appreciated, the phosphorus atom in the phosphodiester linkage is "prochiral". Modifications at the phosphorus, such as is done in methyl phosphonates and phosphorothioates type oligonucleotides, results in essentially chiral structures. Chirality results in the existence of two isomers at each chiral center that may interact differently with cellular molecules. Such an unresolved mixture of isomers may inhibit the transport of the resulting compositions into the intracellular spaces or decrease the affinity and specificity of hybridization to the specific target RNA or DNA. Thus, it is preferred to employ substantially non-ionic, substantially non-chiral entities in lieu of some or all of the phosphodiester bonds. For this purpose, short chain alkyl or cycloalkyl structures especially C2–C4 structures are preferred. The modification of the sugar structure including the elimination of one of the oxygen functionality may permit the introduction of such substantially non-chiral, non-ionic substituents in this position.

In keeping with the goals of the invention, the standard backbone modifications such as substituting S—P, Me—P, MeO—P, or $H_2N$—P (that is phosphorothioates, methyl phosphonates, phosphotriesters or phosphoamidates) for O—P (phosphodiesters) are contemplated. These substitutions are thought in some cases to enhance pyrimidine modified oligonucleotide properties.

The targeting portion of the compositions of the present invention, are preferably oligonucleotie analogs having 5 to about 50 base units. It is more preferred that such functionalities have from 8 to about 40 base units, and even more preferred that from about 12 to 20 base units be employed. Oligonucleotide analogs having about 15 base units are preferable for the practice of certain embodiments of the present invention.

It is desired that the targeting portion be adapted so as to be specifically hybridizable with the preselected nucleotide sequence of the RNA or DNA selected for modulation.

Oligonucleotide analogs particularly suited for the practice of one or more embodiments of the present invention comprise one or more subunits of modified ribose or deoxyribose pyrimidines. The substitutions that may occur at the 5 and 6 positions of the pyrimidine ring may include additions of methyl, hydroxyl, alkoxy, alcohol, benzyl, or phenyl groups. The modifications may also involve the addition of nitro groups, thiol groups, or halogen groups. In the alternative, the modification may be a carbon ring or heteroatom containing ring additions fused to the 5 and 6 positions. The additions that occur at the 5 and 6 positions Imay, but need not be, the same.

These modified bases are linked together and with the rest of the oligonucleotide or oligonucleotide analog through a sugar linking group. The linking group may be any of those structures described herein that are capable of linking sugar moieties of oligonucleotides together to form the targeting portion of the compositions of this invention. It is preferred that these sugar linking groups comprise the phosphodiester structure or a derivative of such. Derivatives of the phosphodiester structure may include substitution of a sulphur, methyl, methyl oxide, or amine group for an oxygen. The sugar phosphate nucleic acid backbone may be modified as a phosphorothioate, methylphosphonate, phosphoamidate or phosphotriester moiety. The phosphodiester linkage may also be replaced by a carbon or ether linkage.

In other embodiments of this invention, a linking moiety has been devised to allow the direct attachment of a modified pyrimidine to the terminal end of the 3'-end of the modified oligonucleotides. Thus, an ester precursor such as a bromomethylketo group, may be attached to the 3'-hydroxyl of a modified pyrimidine nucleoside that has its 5'-hydroxyl protected with a dimethoxytrityl group (a dimethoxytriphenylmethyl group) and,. if necessary, its pyrimidine heterocyclo protected with suitable protecting group, as for instance a benzolate protecting group for the cytosine series of nucleosides. If the required targeting sequence has a terminal 3'-thymine or -cytosine base, the desired modified thymine or cytosine base containing the bromomethylketo linker can be utilized as the first monomer to attach to the control pore glass (CPG) solid support that contains a normal nucleoside attached via its 3'-hydroxyl group. The base sensitive ester linkage attaching the modified pyrimidine to the nucleoside attached to the CPG may be cleaved under the usual concentrated ammonium hydroxide conditions that are utilized to remove the oligonucleotide from the CPG support. This will allow the modified oligonucleotide to have a modified thymine or cytosine at it terminal 3'-end.

Cleavage of oligonucleotides by nucleolytic enzymes require the formation of an enzyme-substrate complex, or in particular a nuclease-oligonucleotide complex. The nuclease enzymes will generally require specific binding sites located on the oligonucleotides for appropriate attachment. If the oligonucleotide binding sites are removed or hindered such that the nucleases will not attach to the oligonucleotides, then nuclease resistant oligonucleotides result. In the case of restriction endonucleases that cleave sequence-specific palindromic double-stranded DNA, certain binding sites such as the ring nitrogen atoms in the 3- and 7-positions of purine bases have been identified as required binding sites. Removal of one or more of these sites or hindering the nuclease approach to these particular positions within the recognition sequence has provided various levels of resistance to the specific nucleases.

A random structure-activity relationship approach was undertaken to discover nuclease resistant antisense oligonucleotides that maintained appropriate hybridization properties. A series of modifications to the 5- and/or 6-positions of the thymine and cytosine ribonucleosides and deoxynucleosides were performed. These modified nucleosides were inserted into sequence-specific oligonucleotides via solid phase nucleic acid synthesis. The novel antisense oligonucleotides were assayed for their ability to resist degradation by nucleases and to possess hybridization properties comparable to the unmodified parent oligo- nucleotide. Preferred embodiments where the 5- and 6- positions of the nucleic acid pyrimidine positions were selected because peripheral modifications and ring modifications such as aza/deaza in these positions are not likely to interfere sterically with required Watson-Crick base pair hydrogen bonding patterns. However, it is believed that profound electronic changes in an ring system result from such seemingly inconsequential heterocyclic changes. These electronic changes may add dipole moments to the aromatic system and/or change directions and strengths of existing dipole moments. Pka strengths will be effected by the electronic perturbation. Peripheral or ring changes as aza/ deaza may change the electrophilicy or nucleophilicy of the ring system such that nucleases, which may require covalent bond formation to a nucleic acid base of an oligonucleotide for their degradative activity, will be inoperative.

During our structure activity relationship studies, it was surprisingly discovered that peripheral and aza/deaza modifications in the 5- and/or 6-positions of the pyrimidines, thymine, cytosine, and uracil provided resistance to nucleases which was comparable to phosphorothioates, known for their nuclease resistance, yet the hybridization properties of the modified oligonucleotides were as good or better than the unmodified parent oligonucleotides.

In some embodiments of this invention modification of the pyrimidines nucleic bases will likely allow about 50% of the antisense oligonucleotide to be modified (two of the four bases available). Modified sequences having all thymines and cytosines replaced with 6-aza-thymine and 6-aza-cytosine (8 out of 15 bases) exhibited nuclease resistance with about a 10% lowering of the $T_m$ compared to the unmodified parent sequence. A preferred combination of nuclease resistance and binding stability results from placing one to three modified pyrimidines at the 3'-end of the oligonucleotide.

The oligonucleotide analogs of this invention can be used in diagnostics, therapeutics, and as research reagents and kits. For therapeutic use the oligonucleotide analog is administered to an animal suffering from a disease effected by some protein. It is preferred to administer to patients suspected of suffering from such a disease with amounts of oligonucleotide analog that are effective to reduce the symptomology of that disease. It is within the realm of a person's skill in the art to determine optimum dosages and treatment schedules for such treatment regimens.

It is generally preferred to apply the therapeutic agents in accordance with this invention internally such as orally, intravenously, or intramuscularly. Other forms of administration, such as transdermally, topically, or intra-lesionally may also be useful. Inclusion in suppositories may also be useful. Use of pharmacologically acceptable carriers is also preferred for some embodiments.

EXAMPLES

EXAMPLE 1

Synthesis of 6-aza-5'-O-(dimethoxytriphenylmethyl)-3'-O-(β-cyanoethyldiisopropylphosphoramidityl)thymidine, i.e., 6-methyl-2-(5'-O-dimethoxytriphenylmethyl-3'-O-β-cyanoethyldiisopropylphosphoramidityl-2'-deoxy-β-D-erythropentofuranosyl)-1,2,4-triazin-3,5(2H, 4H)-dione.

A. Synthesis of 6-Methyl-3,5-bis(trimethylsiloxy)1,2,4-triazine.

A mixture of 6-azathymine (purchased from Aldrich Chemical Co.) (5.0 g, 39.4 mmol), hexamethyldisilazane (HMDS) (15 ml), and chlorotrimethylsilane (TMSCl) (0.5 ml), in a round bottom flask (50 ml) fitted with a condenser and a drying tube, is refluxed by heating in an oil bath (150° C.); $NH_4Cl$ collects as white powder in the condenser. When a clear solution was obtained (~1 hr.), the excess of HMDS/ TMSCl was removed by distillation at 30° C./torr (bath temp 100° C.). The residual oil crystallized on drying under vacuum (0.1 torr), giving 6.57 g ( 61% ) of 6-Methyl-3,5bis(trimethysiloxy)-1,2,4-triazine, mp 43° C.

B. Synthesis of 2-(2-Deoxy-3,5-di-O-p-toluoyl-β-D-erythro-pentofuranosyl)-6-methyl-1,2,4-triazine-3,5(2H, 4H)dione.

A mixture of 6-Methyl-3,5-bis(trimethylsiloxy)-1,2,4-triazine (4.0 g, 14.7 mmol) and 2-deoxy-3,5-di-O-ptoluoyl-α-D-erythro-pentofuranosy chloride (4.8 g, 12.4 mmol) in dry $CHCl_3$ (300 ml) was stirred at room temperature under anhydrous conditions. CuI (2.4 g, 12.4 mmol) was added to the solution and the resulting slurry stirred for 3 hours at ambient temperature at which time thin layer chromatography (TLC) indicated the reaction was complete. The mixture was treated with saturated aqueous $NaHCO_3$ (200 ml), stirred for 15 minutes, and filtered through a pad of celite that had been washed with $CHCl_3$ (2×50 ml). The organic layer was washed with saturated NaCl (200 ml), dried ($MgS_4$) and concentrated to furnish a gummy residue. This material was essentially one spot on TLC. A rapid filtration through a short silica gel column using EtOAc/hexane (1:1) provided several fractions of the desired compounds. Crystallization of the residue from EtOH furnished the product as white needles; 3.64 g (63%), mp 170° C. A second crop was collected from the filtrate (730 mg, 12.6%).

C. Synthesis of 6-azathymidine [2-(2-deoxy-β-D-erythropentofuranosyl)-6-methyl-1,2,4-triazine-3,5(2H, 4H]-dione].

To a mixture of the blocked nucleoside, 2-(2-Deoxy-3,5-di-O-p-toluoyl-β-D-erythro-pentofuranosyl)-6-methyl-1,2, 4-triazine-3,5(2H, 4H)-dione, described above (480 mg, 1 mmol) in absolute MeOH (15 ml), was added dry NaOMe (50 mg) while stirring at room temperature. TLC after one hour indicated complete deblocking of the toluoyl groups. The solution was rendered neutral by addition of one ml of Dowex-50 (hydrogen form) ion-exchange resin. The suspension was filtered and the filtrate was evaporated to dryness under reduced pressure. The residue was dissolved in water (3 ml) and washed with $CHCl_3$ (3×5 ml). The aqueous layer was freeze-dried to provide a hard foam that was further dried over $P_2O_5$ in a vacuum desiccator at 0.1 torr. The compound was obtained in 96% yield (230 mg) and was identical in all respects when compared to the literature values, e.g., UV, NMR TLC and mp.

D. Synthesis of 2-[2-Deoxy-5'-(4,4'-dimethoxytrityl)-β-D-erythro-pentofuranosy]-6-methyl-1,2,4-triazine3,5(2H, 4H)-dione. (6-azathymidine 5'-DMT)

To a stirred solution of 6-azathymidine, synthesized as described above, (2.43 g, 10 mmol) in dry pyridine (100 ml) was added 4,4'-dimethoxytrityl chloride (4.06 g, 12 mmol) and 4-dimethylaminopyridine (120 mg, 1 mmol) at room temperature. The resulting yellow solution was stirred for 6 hours at room temperature, at which time TLC indicated a complete reaction. MeOH (10 ml) was added and the solution was concentrated under vacuum. The residue was dissolved in $CH_2Cl_2$ (200 ml), extracted with saturated $NaHCO_3$ (100 ml) followed by sat. NaCl (100 ml), and then dried ($MgSO_4$). The filtrate and washings were combined and concentrated to provide a gummy residue that was purified by silica gel chromatography using EtOA$_c$/triethylamine (99/1) for elution. Appropriate fractions were pooled and concentrated to furnish a white foam (3.82 g 70%); $^1$H NMR ($CDCl_3$) $\delta 6.56$ (t, 1H, $C_1$, H) and other protons.

E. Synthesis of 2-[2'-Deoxy-5'-(4,4'-dimethoxytrityl)-β-D-erythro-pentofuranosyl]-6-methyl-,1,2,4-triazine-3,5(2H, 4H)-dione 3'-O-N,N-diisopropyl-β-cyanoethylphosphoramidite.

To a stirred solution of 6-azathymidine 5'-DMT, synthesized as described above, (1.63 g, 3 mmol) in dry THF (50 ml) was added diisopropylethylamine (1.56 ml, 9 mmol) and solution was cooled to 0° C. N,N-Di-isopropyl-β-cyanoethylphosphonamidic chloride (1.42 ml, 6 mmol) was added dropwise to the above solution over a period of 15 min. The reaction mixture was then stirred at room temperature for 2 hours. Ethyl acetate (100 ml, containing 1% triethylamine) was added and the solution washed with saturated NaCl solution (2×100 ml). The organic layer was dried ($MgSO_4$) and the solvent removed under vacuum to furnish a gummy residue. The product was purified by silica gel column chromatography using EtOAc/triethylamine (99/1, V/V) for elution. Pooling and concentration of appropriate fractions furnished a white foam 1.41 g (66%); $^1$H NMR ($CDCl_3$) $\delta 6.65$ (m, 1, $C_1$H), 10.2 (brs, 1, NH) and other protons.

Other species of 6-aza-pyrimidines may also be synthesized using this procedure including 6-aza-2'deoxycytidine (6-Aza dC), 6-aza-2'-deoxyuridine (6-Aza dU), 6-aza-5-methylcytidine (6-Aza-5-Methyl C), 6-aza-5bromouridine (6-Aza-5-Bromo U), 5-fluorocytidine (5-Fluoro C), and 5-bromocytidine (5-Bromo C). In addition, 5-azauridine can be similarly synthesized from the starting material 1,3,5-Triazin-2,4(1H, 3H)-dione (Sigma Chemical).

Example 2

Procedure for the conversion of 5- and/or 6-modified thymine and cytosine 2'-deoxyribonucleoside-5'-DMT-3'-phosphoramidites into oligonucleotides.

Table I depicts the protocol for the synthesis of DNA on CPG supports. Prior to synthesis 5- and/or 6-modified thymine, cytosine 5'-dimethoxytriphenylmethyl -2'-deoxyribonucleoside, or generally any nucleoside with modifications in the heterocycle and/or sugar may be attached to the 5'-hydroxyl of nucleosides bound to CPG support in order to attach such a modified nucleoside at the very 3' end of the oligonucleotide sequence.

The modified thymidines or 2'-deoxycytidines that will reside in the terminal 3'-position of certain antisense oligonucleotides are protected by their 5'-DMT (the cytosine 4-exocyclic amino is benzoylated) and treated with trifluoroacetic acid/bromoacetic acid mixed anhydride in pyridine and dimethylaminopyridine at 50° C. for five hours. The solution is evaporated under reduced pressure to a thin syrup that is dissolved in ethyl acetate and passed through a column of silica gel. The homogenous fractions were collected and evaporated to dryness. A solution of 10 ml of acetonitrile, 10 micromoles of the 3'-O-bromomethylester modified pyrimidine nucleoside, and one ml of pyridine/dimethylaminopyridine (1:1) is syringed slowly (60 to 90 sec) through a one micromole column of CPG thymidine (Applied Biosystems, Inc.) that had previously been treated with acid according to standard conditions to afford the free 5'-hydroxyl group. Other nucleoside bound CPG columns could be employed. The eluent is collected and syringed again through the column. This process is repeated three times. The CPG column is washed slowly with 10 ml of acetonitrile and then attached to an ABI 380B nucleic acid synthesizer. Oligonucleotide synthesis as described in Table 1 is now initiated. The standard conditions of concentrated ammonium hydroxide deprotection that cleaves the thymidine ester linkage from the CPG support also cleaves the 3', 5' ester linkage connecting the pyrimidine modified nucleoside to the thymidine that was initially bound to the CPG nucleoside.

Standard synthesis of DNA may also be completed according to Table I, on CPG LCAA using 1–10 micromoles of nucleoside on the support. Polymer bound nucleosides were purchased from Applied Biosystems, Inc. The synthesis was accomplished using an automated synthesizer (ABI 380B) with a continuous flow (3.0–3.5 ml/min). Phosphoramidite condensations were completed under dry nitrogen. At the completion of the synthesis, oligonucleotide cleavage and deprotection were effected by treatment with concentrated ammonia at 55° C. for 24 hours. The purity and size of the final products were confirmed by electrophoretic analysis on polyacrylamide gels.

TABLE I

Protocol for synthesis of DNA on CPG supports
(1–10 micromole scale)

| Step (ml) | Reagent or Solvent Mixture | Time (min:sec) | Vol |
|---|---|---|---|
| 1 | Dichloroethane | 1:30 | 5.0 |
| 2 | 3% DCA in dichloroethane | 1:30 | 5.0 |
| 3 | Dichloroethane | 1:00 | 3.5 |
| 4 | Acetonitrile | 2:00 | 5.0 |
| 5 | Condensation-Phosphoramidite In line mixing - 20 micromoles of phosphoramidite/$CH_3CN$ and 3% Tetrazole in $CH_3CN$ | 1:00 | 3.5 |
|   | Recycling | 1:00 | — |
| 6 | Oxidation - 0.01M Iodine in a mixture of $CH_3CN$:$H_2O$:2-lutidine | 0:20 | 1.0 |
| 7 | Capping (in line mixing) a) 20% (AcO)$_2$ in $CH_3CN$:2-lutidine (80:20) b) 3% DMAP in $CH_3CN$ | 1:00 | 3.5 |
|   | Recycling | 1:00 | — |

The synthesis cycles are combined into four basic steps: 1) acidic treatment to remove 5'-dimethoxytrityl protecting groups; 2) condensation of the polymer bound nucleoside with a nucleoside-3'-diisopropylphosphoramidite for DNA and 3) oxidation, using iodine and water in acetonitrile, to convert the phosphite linkage into a phosphate linkage; and 4) capping with acetic anhydride and DMAP to block off unreacted sites and to remove residual moisture.

After assembly of the desired sequence by the automated synthesizer, the final product was cleaved from the polymer, deprotected and isolated.

The deprotection was accomplished by treatment of the polymer support with ammonium hydroxide ($NH_4OH$) at 55° C. for 20 hours. The crude material was purified by tritylon HPLC. Detritylation was accomplished with 3% ethylacetate followed by extractions with ethylacetate. Purification was accomplished by sodium chloride/ethanol precipitation (2X) and HPLC. All of the above mixed sequences were characterized by kinasing the samples and sizing them.

Example 3

Synthesis of the 6-aza-thymine-modified oligonucleotides, listed below, was accomplished according to Example 2 wherein the procedure for the attachment of 5-and/or 6- modified thymine or cytosine 5'-dimethoxytriphenylmethyl-2'-deoxyribonucleoside to the 5' hydroxyl of nucleosides bound to a CPG support was provided. The phosphoramidites synthesized according to the method provided in Example i are incorporated into oligonucleotides having the following sequences that are useful due to their nuclease resistant characteristics.

| OLIGONUCLEOTIDES HAVING 6-AZA-THYMIDINE (T') SUBSTITUTIONS | |
|---|---|
| SEQUENCE | SUBSTITUTION POSITION(S) |
| T'T'T'T'T'T'T'T'T'T'T'T'T'T'[1] | 1–14 |
| AT'AT'AT'AT'AT'AT'AT'AT'[2] | 2,4,6,8,10,12,14 |
| T'CCAGGT'GT'CCGCAT[3] | 1,7,9 |
| T'CCAGGT'GT'CCGCAT'C[4] | 1,7,9,15 |
| T'CCAGGT'GT'CCGCAT'C[1,7,9] | 1,7,9 |
| T'CCAGGTGTCCGCAT'C[5] | 1,15 |
| TCCAGGTGTCCGCAT'C[6] | 15 |
| T'CCAGGTGTCCGCATC[7] | 1 |
| T'CCAGGT'GTCCGCATC[8] | 1,7 |
| TCCAGGT'GT'CCGCATC[9] | 7,9 |
| T'CCAGGT'GT'CCGT'T'T'C[10] | 1,7,9,13,14,15 |
| T'CCAGGT'GT'CCGT'sT'sT'sC[11] | 1,7,9,13,14,15 |
| CGACT'AT'GCAAGT'AC[12] | 5,7,13 |
| CGACTATGCAAT'T'T'C[13] | 12,13,14 |
| T'T'T'CTATGCAAGTAC[14] | 1,2,3 |
| GT'CCAT'GT'CGT'ACGC[15] | 2,6,8,11 |
| ACCGAGGT'CCAT'GT'CGT'ACGC[16] | 8,12,14,17 |
| AC'C'GAGGT'C'C'AT'GT'C'GT'AC'GC[17] | 8,12,14,17 |
| CCT'T'CCCCT'C[18] | 3,4,9 |

[1]SEQ ID NO: 1
[2]SEQ ID NO: 2
[3]SEQ ID NO: 3; selected sequence from 5 lipoxgenase genome
[4]SEQ ID NO: 4
[5]SEQ ID NO: 5
[6]SEQ ID NO: 6
[7]SEQ ID NO: 7
[8]SEQ ID NO: 8
[9]SEQ ID NO: 9
[10]SEQ ID NO: 10
[11]SEQ ID NO: 11; P of the phosphodiester bond is replaced by an S at the 13, 14, and 15 positions
[12]SEQ ID NO: 12; selected sequence from the papilloma virus genomes
[13]SEQ ID NO: 13; selected sequence from the papilloma virus genomes
[14]SEQ ID NO: 14; selected sequence from the papilloma virus genomes
[15]SEQ ID NO: 15; selected sequence from the herpes simplex virus genomes
[16]SEQ ID NO: 16; selected sequence from the herpes simplex virus genomes
[17]SEQ ID NO: 17; selected sequence from the herpes simplex virus genomes; 6 aza-cytidine substitutions at the 2, 3, 9, 10, 15 and 19 positions
[18]SEQ ID NO: 18; sequence found especially effective as a triplex

Example 4

Synthesis of 6-aza-cytosine modified oligonucleotides, listed below, was accomplished according to Example 2 wherein a method for the conversion of 5-and/or 6- modified thymine and cytosine 2' deoxyribonucleoside-5-DMT-3'-phosphoramidites into oligonucleotides is provided. The phosphoramidites synthesized according to the method specified in Example 1 are substituted for wild type bases of the oligonucleotides of the following sequences in order to increase nuclease resistance.

| OLIGONUCLEOTIDES HAVING 6-AZA-CYTIDINE SUBSTITUTIONS | |
|---|---|
| SEQUENCE | SUBSTITUTION POSITION(S) |
| C'C'C'C'C'C'C'C'C'C'C'C'C'C'[1] | 1–14 |
| C'C'C'AGGTGTCCGCATC[2] | 1,2,3 |
| TCCAGGTGTCCGCATC[3] | 10,11 |
| TCCAGGTGTCCGC'C'C'[4] | 13,14,15 |
| TCCAGGTGTCCGCC'C'[5] | 14,15 |
| CGACTATGCAAC'C'C'[6] | 12,13,14 |
| C'C'C'CTATGCAAGTAC[7] | 1,2,3 |
| C'GACTATGC'AAGTAC[8] | 1,4,9 |
| AC'C'GAGGTC'C'ATGTC'GTAC'GC[9] | 2,3,9,10,15,19 |
| AC'C'GAGGT'C'C'AT'GT'C'GT'AC'GC[10] | 2,3,9,10,15,19 |

[1]SEQ ID NO: 19
[2]SEQ ID NO: 20; sequence selected from 5 lipoxygenase genome
[3]SEQ ID NO: 21
[4]SEQ ID NO: 22
[5]SEQ ID NO: 23
[6]SEQ ID NO: 24; sequence selected from papilloma virus genomes
[7]SEQ ID NO: 25
[8]SEQ ID NO: 26
[9]SEQ ID NO: 27
[10]SEQ ID NO: 17; 6 aza-thymidine substitutions at positions 8, 12, 14 and 17

Example 5

Conversion of 5- and/or 6-position modified thymines to the corresponding thymidines (deoxyribosylation).

The thymine analogs are trimethylsilylated under various standard conditions such as hexamethyldisilazane (HMDS) and an acid catalyst (i.e., ammonium chloride) and then treated with 3,5–0-ditoluoyl-2-deoxy-α-D-erythro-pentofuranosyl chloride in the presence a variety of Lewis acid catalysts (i.e., stannic chloride, iodine, boron tetrafluoroborate, etc.). A specific procedure has recently been described by J. N. Freskos, *Nucleosides & Nucleotides,* 8:1075–1076 (1989), in which copper (I) iodide is the catalyst employed.

Example 6

Synthesis of 6-aza-5-bromo-5'-O-(dimethoxytriphenylmethyl-)-3'-O-(β-cyanoethyldiisopropylphosphoramidityl)-2'-deoxyuridine, i.e., 6-bromo-2-(5'-O-[dimethoxytriphenylmethyl]-3-O-[β-cyanoethyldiisopropylphosphoramidityl]2'-deoxy-β-erythro-pentofuranosyl)-1,2,4-triazin-3,5-(2H, 4H)-dione.

The required heterocycle, 6-Bromo-1,2,3-triazin-3,5(2H, 4H)-dione, was prepared according C. Cristescu, *Rev. Roumaine Chim.* 20:1287(1975). Deoxyribosylation of this material and subsequent. DMT and amidite chemistry is performed according to the procedures set forth in Examples 1, 2 and 5.

Example 7

Conversion of 5- and/or 6-position modified thymidines to the corresponding 2' deoxycytidines (chemical conversion of an pyrimidine type 4-keto group to an 4-amino group).

The 3', 5'-sugar hydroxyls of the modified thymidine types are protected by acyl groups such as toluoyl, benzoyl, p-nitrobenzoyl, acetyl, isobutyl, trifluoroacetyl, etc. using standards conditions of the acid chlorides or anhydrides and pyridine/dimethylaminopyridine solvent and catalysts. The protected nucleoside is chlorinated with thionyl chloride or phosphoryl chloride in pyridine or other appropriate basic solvents. The pyrimidine type 4-chloro groups are next displaced with ammonium in methanol. Deprotection of the sugar hydroxyls also takes place. The amino group is benzoylated by the standard two-step process of complete benzylation (sugar hydroxyls and amino group) and the acyls are selectively removed by aqueous sodium hydroxide solution. Alternatively, the in situ process of first treating the nucleoside with chlorotrimethylsilane and base to protect the sugar hydroxyls from subsequent acylation may be employed. Another conversion approach is to replace the pyrimidine type 4-chloro group with an 1,2,4-triazolo group that remains intact throughout the oligonucleotide synthesis on the DNA synthesizer and is displaced by ammonium during the ammonium hydroxide step that removes the oligonucleotide from the CPG support and deprotection of the heterocycles. Furthermore, in many cases the pyrimidine type 4-chloro group can be utilized as just described and replaced at the end of the oligonucleotide synthesis. 5-aza-cytidine and 5-nitro-cytidine may accordingly be obtained from its uridine analog. Likewise, 4-chloro-5-methylmercaptocytidine is synthesized as described.

Example 8

Synthesis of 6-aza-5-bromo-5'-O-(dimethoxytriphenylmethyl)-3'-O-(β-cyanoethyldiisopropylphosphoramidityl)-2'-deoxycytidine, i.e., 5-amino-6-bromo-2-(5'-O-dimethoxytriphenylmethyl-3'-O-β-cyanoethyldiisopropylphosphoramidityl-2'-deoxy-β-D-erythro-pentofuranosy)-1,2,4-triazin-3(2H)-one.

This monomer is prepared by the conversion of the deoxyribosylated 6-Bromo-1,2,3-triazin-3,5(2H, 4H)-dione (according to Example 7) to the 2'-deoxycytidine analog according to Example 5.

Example 9

1. Synthesis of 5-Trifluoro-5'-O-(dimethoxytriphenylmethyl)-3'-O-(β-cyanoethyldiisopropylphosphoramidityl)-2'-deoxyuridine, i.e., 1-(5'-[4,4'-dimethoxytrityl]-2'-deoxy-β-D-erythro-pentofuranosyl)5,5,5-trifluorothymine.

Trifluorothymidine (1, 2.0 g), (purchased from PCR, Inc., Gainsville, Fla.), was twice coevaporated with pyridine and then dissolved in anhydrous pyridine (100 ml) under an argon atmosphere. 4,4'-Dimethylaminopyridine (50 mg) and 4,4'-dimethoxytrityl chloride (2.74 g) were successively added to the solution which was then stirred at room temperature for 6 hr. The reaction mixture was treated with 100 ml of water then repeatedly extracted with diethyl ether (4×100 ml). The ether extracts were pooled, dried over magnesium sulfate, filtered and then evaporated in vacuo to afford an orange gum. This gum was coevaporated with toluene (3×25) ml) and then chromatographed on 120 g silica gel using ethyl acetate/hexanes/triethylamine (49/49/2, v/v) as eluent. The appropriate fractions were pooled and evaporated to yield 0.77 g (19%) of a solid foam. 'H-NMR (DMSO-d6) δ8.05 (s, 1H, H-6); 7.4–6.7 (2 m, 13H, aromatic); 6.05 (t, 1H, H-1').

2. Synthesis of 1-(5'-[4,4'-Dimethoxytrityl]-2'-deoxy-β-D-erythro-pentofuranosyl)-5,5,5-trifluorothymine-3'-O-N,N-diisopropyl-β-cyanoethyl phosphoramidite (3).

To a stirred solution of 5-Trifluoro-5'-O-(dimethoxytriphenylmethyl)-3'-O-(β-cyanoethyldiisopropylphosphoramidityl)-2'-deoxyuridine, i.e., 1-(5'-[4,4'-dimethoxytrityl] -2'-deoxy-β-D-erythro-pentofuranosyl) 5,5,5-trifluorothymine (2) (0.70 g, 1.2 mMol) in anhydrous THF was added diisopropylethyl amine (1.0ml) under an argon atmosphere. To this solution was added N,N-diisopropyl-cyanoethylphosphoramidic chloride (0.33ml, 1.44 mMol) dropwise over a period of 5 min. The mixture was stirred at room temperature for 3 hr. At the end of this time, the reaction mixture was evaporated to dryness in vacuo and the gummy residue that resulted was dissolved in $CH_2Cl_2$ (75 ml). The solution was washed with satd. $NaHCO_3$ (2×35 ml) and brine (35 ml). The organic layer was separated, dried over magnesium sulfate, filtered and evaporated in vacuo to afford a colorless gum. This material was chromatographed on 60 g of silica gel using $CHCl_3$/triethylamine (99/1, v/v) as eluent. The appropriate fractions were pooled and evaporated to afford a colorless foam (0.6 g, 67%). 'H-NMR (DMSO-d6): δ8.15 (s, 1H, H-6); 7.4–6.8 (1 m, 13H, aromatic); 6.05 (t, 1H, H-1'). This phosphoramidite may be subsequently incorporated into oligonucleotides according to the procedure set forth in Example 2. Some examples follow.

| OLIGONUCLEOTIDES HAVING 5-TRIFLUOROMETHYL-2'-DEOXYURIDINE SUBSTITUTIONS | |
|---|---|
| SEQUENCE | SUBSTITUTION POSITION(S) |
| T'CCAGGTGTCCGCATC[1] | 1 |
| T'CCAGGT'GTCCGCATC[2] | 1,7 |
| T'CCAGGT'GT'CCGCATC[3] | 1,7,9 |
| TCCAGGT'GT'CCGCATC[4] | 7,9 |
| TCCAGGTGTCCGCAT'C[5] | 15 |
| CGACTATGCAATT'T'C[6] | 12,13,14 |
| T'T'T'CTATGCAAGTAC[7] | 1,2,3 |
| ACCGAGGT'CCAT'GT'CGT'ACGC[8] | 8,12,14,17 |

[1]SEQ ID NO: 28
[2]SEQ ID NO: 29
[3]SEQ ID NO: 30
[4]SEQ ID NO: 31
[5]SEQ ID NO: 32
[6]SEQ ID NO: 33; sequence selected from papilloma virus genomes
[7]SEQ ID NO: 34
[8]SEQ ID NO: 35; sequence selected from herpes simplex virus genomes Example 10

5-Fluoro-5'-O-(dimethoxytriphenylmethyl)-3'-O-(β-cyanoethyldiisopropylphosphoramidityl)-2'-deoxyuridine was purchased from Glen Research Corporation. This has previously been inserted into oligonucleotides. J. F. Habener, et al., *Proceedings of the National Academy of Sciences of the U.S.A.*, 85:1735–1739 (1988). Some examples are listed below.

| OLIGONUCLEOTIDES HAVING 5-FLUORO-2'-DEOXYURIDINE SUBSTITUTIONS | |
|---|---|
| SEQUENCE | SUBSTITUTION POSITION(S) |
| TTTTTTTTTTTTTTT[1] | 1–15 |
| TCCAGGTGTCCGCAT'C[2] | 15 |
| TCCAGGT'T'CCGCAT'C[3] | 7,9 |
| T'CCAGGT'GT'CCGCAT'C[4] | 1 |
| T'CCAGGTGTCCGT'T'T'C[5] | 13,14,15 |
| T'CCAGGT'GT'CCGCAT'C[6] | 1,7,9,15 |

[1]SEQ ID NO: 36
[2]SEQ ID NO: 37; sequence selected from 5 lipoxygenase genome
[3]SEQ ID NO: 38
[4]SEQ ID NO: 39
[5]SEQ ID NO: 40
[6]SEQ ID NO: 41

Example 11

5-Bromo-5'-O-(dimethoxytriphenylmethyl)-3'-O-(β-cyanoethyldiisopropylphosphoramidityl)-2'-deoxyuridine, purchased from Glen Research Corporation, was incorporated into oligonucleotide sequences during synthesis according to the procedure set forth in Example 2.

OLIGONUCLEOTIDES WITH 5-BROMO-2'-DEOXYURIDINE SUBSTITUTIONS

| SEQUENCE | SUBSTITUTION POSITION(S) |
|---|---|
| T'T'T'T'T'T'T'T'T'T'T'T'T'T'T'[1] | 1–15 |
| TCCAGGTGTCCGCAT'C[2] | 15 |
| T'CCAGGTGTCCGCATC[3] | 1 |
| TCCAGGT'GT'CCGCATC[4] | 7,9 |
| TCCAGGTGTCCGT'T'T'C[5] | 13,14,15 |
| T'CCAGGT'GT'CCGCAT'C[6] | 1,7,9,15 |

[1]SEQ ID NO: 42
[2]SEQ ID NO: 43; sequence selected from 5 lipoxygenase genome
[3]SEQ ID NO: 44
[4]SEQ ID NO: 45
[5]SEQ ID NO: 46
[6]SEQ ID NO: 47

Example 12

Synthesis of 5-bromo-2'-deoxycytidine-modified oligonucleotides, listed below, was accomplished according to the procedure set forth in Example 2.

OLIGONUCLEOTIDES WITH 5-BROMO-2'-DEOXYCYTIDINE (C') SUBSTITUTIONS

| SEQUENCE | SUBSTITUTION POSITION(S) |
|---|---|
| C'C'C'C'C'C'C'C'C'C'C'C'C'C'C'[1] | 1–15 |
| C'CCAGGTGTCCGCAT'C[2] | 1 |
| TCCAGGTGTCCGCAC'C[3] | 15 |
| TCCAGGTGTC'C'GCATC[4] | 10,11 |
| TCCAGGTGTCCGC'C'C'C[5] | 13,14,15 |
| TC'C'AGGTGTC'C'GC'ATC[6] | 2,3,10,11,13 |

[1]SEQ ID NO: 28
[2]SEQ ID NO: 49; sequence selected from 5 lipoxygenase genome
[3]SEQ ID NO: 50
[4]SEQ ID NO: 51
[5]SEQ ID NO: 52
[6]SEQ ID NO: 53

Example 13

Synthesis of 5-methyl-2'-deoxycytidine-modified oligonucleotides, listed below, was accomplished according to the procedure set forth in Example 2 by substituting 5 methyl-2' deoxycytidine (Glen Research Corporation) for wild type cytidine bases.

OLIGONUCLEOTIDES HAVING 5-METHYL-2'-DEOXYCYTIDINE (C') SUBSTITUTIONS

| SEQUENCE | SUBSTITUTION POSITION(S) |
|---|---|
| C'C'C'C'C'C'C'C'C'C'C'C'C'C'C'[1] | 1–15 |
| C'CCAGGTGTCCGCAT'C[2] | 1 |
| TCCAGGTGTCCGCAC'C[3] | 15 |
| TCCAGGTGTC'C'GCATC[4] | 10,11 |
| TCCAGGTGTCCGC'C'C'C[5] | 13,14,15 |
| TC'C'AGGTGTC'C'GC'ATC[6] | 2,3,10,11,13 |

[1]SEQ ID NO: 54
[2]SEQ ID NO: 55; sequence selected from 5 lipoxygenase genome
[3]SEQ ID NO: 56
[4]SEQ ID NO: 57
[5]SEQ ID NO: 58
[6]SEQ ID NO: 59

Example 14

Synthesis of 5-iodo-2'-deoxyuridine-modified oligonucleotides, listed below, was accomplished according to the procedure set forth in Example 2 by substituting 5-iodo-2'-deoxyuridine (Glen Research Corporation) for wild type uridine bases.

OLIGONUCLEOTIDES HAVING 5-IODO-2'-DEOXYURIDINE SUBSTITUTIONS

| SEQUENCE | SUBSTITUTION POSITION(S) |
|---|---|
| T'T'T'T'T'T'T'T'T'T'T'T'T'T'T'[1] | 1–15 |
| TCCAGGTGTCCGCAT'C[2] | 15 |
| T'CCAGGTGTCCGCATC[3] | 1 |
| TCCAGGT'GT'CCGCATC[4] | 7,9 |
| TCCAGGTGTCCGT'T'T'C[5] | 13,14,15 |
| T'CCAGGT'GT'CCGCAT'C[6] | 1,7,9,15 |

[1]SEQ ID NO: 60
[2]SEQ ID NO: 61; sequence selected from 5 lipoxygenase genome
[3]SEQ ID NO: 62
[4]SEQ ID NO: 63
[5]SEQ ID NO: 64
[6]SEQ ID NO: 65

Example 15

The synthesis of 5-iodo-5'-O-(dimethoxytriphenyl-methyl)-3'-(β-cyanoethyldiisopropylphosphoramidityl)-2'-deoxycytidine is accomplished by the utilization of the procedures set forth in Examples 2, and 7.

Example 16

Synthesis of 5-chloro-5'-O-(dimethoxytriphenyl-methyl)-3'-(β-cyanoethyldiisopropylphosphoramidityl)-2'-deoxyuridine.

5-Chlorouracil is commercially available from Aldrich Chemical Company. This material is converted to the title phosphoramidite according to the procedures set forth in Examples 1, 2 and 5.

Example 17

The synthesis of 5-chloro-5'-O-(dimethoxytriphenyl methyl)-3'-O-(β-cyanoethyldiisopropylphosphoramidityl)-2'-deoxycytidine is accomplished according to the procedures set forth in Examples 2 and 7.

Example 18

Synthesis of 5-nitro-5'-O-(dimethoxytriphenyl-methyl)-3'-O -(β-cyanoethyldiisopropylphosphoramidityl)-2'-deoxyuridine.

5-Nitrouracil is commercially available from Aldrich Chemical Company. This material is converted to the title phosphoramidite according to Examples 1, 2 and 5.

Example 19

Synthesis of 5-(2,4-dinitrophenylmercapto-5'-O-(dimethoxytriphenylmethyl)-3'-O-(β-cyanoethyldiisopropyl-aminophosphinyl)-2'-deoxyuridine.

The 5-mercapto-2'-deoxyuridine, obtained from the procedure of Fox et al., *Journal of the American Chemical Society* 81:178 (1959), is converted to the 2,4-dinitrophenylsulfinyl derivative by treatment with an equivalent of sodium hydride and 2,4-dinitrophenylfluoride. This material is converted to the 5'-DMT-3'-phosphoramidite as described in procedures set forth in Example 1.

Example 20

Synthesis of 4-chloro-5-(2,4-dinitrophenylmercapto)-5'-O-(dimethoxytriphenylmethyl)-3'-O-(b-cyanoethyldiisopropylaminophosphinyl)-2'-deoxycytidine.

The 5-mercapto-2'-deoxyuridine, obtained from the procedure of Fox et al., *Journal of the American Chemical Society* 81:178 (1959), is converted to the 2,4-dinitrophenylsulfinyl derivative by treatment with an equivalent of sodium hydride and 2,4-dinitrophenylfluoride. This material is acetylated, chlorinated, and converted to the 5'-DMT-3'-phosphoramidite as described in Example 1 and 5.

Example 21

Synthesis of 5-methylmercapto-5'-O-(dimethoxytriphenylmethyl)-3'-O-(β-cyanoethyldiisopropylaminophosphinyl)-2'-deoxyuridine.

The 5-mercapto-2'-deoxyuridine, obtained from the procedure of Fox et al., *Journal of the American Chemical Society* 81:178 (1959), is converted to the methyl derivative by treatment with an equivalent of sodium hydride and methyliodide. This material is converted to the 5'-DMT-3'-phosphoramidite as described in procedures set forth in Example 1.

Example 22

The ability of pyrimidine modified oligonucleotides to hybridize to their complementary RNA or DNA sequences was determined by thermal melting analysis. The RNA complement was synthesized from T7 RNA polymerase and a template-promoter of DNA synthesized with an Applied Biosystems, Inc. 380B synthesizer. The RNA species was purified by ion exchange using FPLC (LKB Pharmacia, Inc.). Either natural antisense oligonucleotides or those containing pyrimidine modifications at specific locations were added to either the RNA or DNA complement at stoichiometric concentrations and the absorbance (260 nm) hyperchromicity upon duplex to random coil transition was monitored using a Gilford Response II spectrophotometer. These measurements were performed in a buffer of 10 mM Na-phosphate, pH 7.4, 0.1 mM EDTA, and NaCl to yield an ionic strength of 1 either 0.1M or 1.0M. Data was analyzed by a graphic representation of 1/Tm vs ln[Ct], where [Ct] was the total oligonucleotide concentration. From this analysis the thermodynamic parameters were determined. The results of certain of these tests are shown in Table II.

TABLE II

MELTING TEMPERATURE (Tm) DATA ON MODIFIED OLIGONUCLEOSIDES
5' TCC AGG TGT CGG CAT C 3'
position 1 to 16 reading from 5' to 3'

| Modified Pyrimidine | Site(s) of Modification | Tm (°C.) |
|---|---|---|
| 6-Aza T | 1 | 62.8 |
|  | 15 | 62.0 |
|  | 7,9 | 58.2 |
|  | 1,7,9,15 | 54.5 |
| 6-aza dC | 2 | 63.0 |
|  | 2,3 | 59.8 |
|  | 10,11 | 51.0 |
| 6-Me dU | 1 | 63.2 |
|  | 15 | 62.5 |
|  | 7,9 | 55.7 |
|  | 1,7,9,15 | 52.3 |
| 5,6-DiMe dU | 15 | 60.3 |
|  | 7,9 | 54.7 |
|  | 1,7,9,15 | 52.5 |
| 5-Iodo dU | 1 | 63.5 |
|  | 15 | 63.3 |
|  | 7,9 | 63.3 |
|  | 1,7,9,15 | 61.5 |
| 5-Bromo dU | 1 | 63.5 |
|  | 15 | 63.3 |
|  | 7,9 | 63.3 |
|  | 1,7,9,15 | 61.5 |
| 5-Fluoro dU | 1 | 63.2 |
|  | 15 | 63.2 |
|  | 7,9 | 65.0 |
|  | 1,7,9,15 | 63.7 |
| 5-Bromo dC | 10,11 | 65.8 |
|  | 2,3,10,11,13 | 68.0 |
| 5-Me dC | 10,11 | 65.3 |
|  | 2,3,10,11,13 | 67.0 |

TABLE III

EFFECTS OF PYRIMIDINE MODIFICATIONS ON DUPLEX STABILITY AND SPECIFICITY

| Compound | Stability vs DNA Target | Specificity vs DNA Target |
|---|---|---|
| natural DNA | 0 | +4.2 |
| 6-Aza T | +0.6 | +3.7 |
| 6-Aza dC | +1.9 | +6.0 |
| 6-Me dU | +1.3 | +3.0 |
| 5,6-DiMe dU | +1.1 | +1.5 |
| 5-Iodo dU | +0.3 | — |
| 5-Bromo dU | −0.3 | +4.9 |
| 5-Fluoro dU | −0.2 | +4.4 |
| 5-Bromo dC | −0.1 | +6.5 |
| 5-Methyl dC | −0.2 | +6.3 |

The ability of the pyrimidine modified antisense oligonucleotides to hybridize with specificity to the targeted mRNA was shown by Northern blot analysis of purified target mRNA in the presence of total cellular RNA. Target mRNA was synthesized from a vector containing the cDNA for the target mRNA located downstream from a T7 RNA polymerase promoter. Synthesized mRNA was electrophoresed in an agarose gel and transferred to a suitable support membrane (i.e., nitrocellulose). The support membrane was blocked and probed using [$^{32}$P]-labeled antisense oligonucleotides.

The stringency was determined by replicate blots and washing at either elevated temperatures or decreased ionic strength of the wash buffer. Autoradiography was performed to assess the presence of heteroduplex formation and the autoradiogram quantitated by laser densitometer (LKB Pharmacia, Inc.).

The specificity of hybrid formation was determined by isolation of total cellular RNA by standard techniques and its analysis by agarose electrophoresis, membrane transfer and probing with the labeled pyrimidine modified oligonucleotides. Stringency was predetermined for the unmodified antisense oligonucleotides and the conditions used such that only the specifically targeted mRNA was capable of forming a heteroduplex with the pyrimidine modified oligonucleotide.

Example 23

Natural, phosphorothioate, and pyrimidine modified oligonucleotides were assessed for their resistance to serum nucleases by incubation of the oligonucleotides in media containing various concentrations of fetal calf serum (FCS) or adult human serum. Labeled oligonucleotides were incubated for various times, treated with protease K and then analyzed by gel electrophoresis on 20% polyacrylamide-urea denaturing gels and subsequent autoradiography. Autoradiograms were quantitated by laser densitometry. Based upon the location of the modifications and the known length of the oligonucleotide, it was possible to determine the effect on nuclease degradation by the particular pyrimidine modification For the cytoplasmic nucleases, a HL60 cell line was used A post-mitochondrial supernatant was prepared by differential centrifugation and the labeled oligonucleotides were incubated in this supernatant for various times. Following the incubation, oligonucleotides were assessed for degradation as outlined above for serum nucleolytic degradation Autoradiography results were quantitated for comparison of the unmodified, the phosphorothioates, and the pyrimidine modified oligonucleotides.

Evaluation of the resistance of natural and pyrimidine-modified oligonucleotides to specific nucleases (i.e., endonucleases, 3',5'-exo-, and 5',3'-exonucleases) was done to determine the exact effect of the modifications on degradation. Modified oligonucleotides were incubated in defined reaction buffers specific for various selected nucleases. Following treatment of the products with proteinase K, urea was added and analysis on 20% polyacrylamide gels containing urea was done. Gel products were visualized by staining using Stains All (Sigma Chemical Co.). Laser densitometry was used to quantirate the extent of degradation. The effects of the pyrimidine modifications were determined for specific nucleases and compared with the results obtained from the serum and cytoplasmic systems.

In one such test about 1 mg/ml of modified pyrimidine hearing oligonucleotides were incubated at 37° C. in DMEM supplemented with 10% heat activated FCS. At various time points aliquots were removed and mixed in an equal volume of 9M urea/1 x TBE buffer and frozen at −20° C. The samples were analyzed by polyacrylamide electrophoresis (20% PA/7M urea) and visualized by Stains All reagent and subjected to quantitation using an LKB laser densitometer. Integrations of peaks representing the full length oligonucleotide and the n-1 oligonucleotide were made. The % degradation was calculated for each time point by comparison to the time point 0 of sample. The data was graphed and graphic estimations for $T_{1/2}$ of the modified oligonucleotide was made by comparison to the natural unmodified oligonucleotide. Utilizing 6-aza T containing oligonucleotide it was found that such 6-aza T modified oligonucleotide exhibited greater stability towards nucleolytic degradation. For the 6-aza T compounds, increasing the number of modification increased the stability towards degradation in FCS. Furthermore, the best results were obtained when 6-aza T was used as a 3-terminus cap. An oligonucleotide containing such a 3'-terminus cap provided protection from 3-5 exonucleolytic degradation compared to a natural oligonucleotide. T½ increased from 20 min. for a natural oligonucleotide to a T½ of 4 h for the modified oligonucleotide. This represented a 12-fold decrease in the susceptibility of oligonucleotide to degradation in presence of FCS. The results of this test suggests that FCS, which is known to hydrolyse natural unmodified oligonucleotides from the 3 end, does not recognize a block of three 6-aza T as an appropriate substrate. Such lack of recognition decreases the hydrolysis of modified oligonucleotide considerably.

Example 24

Ribonuclease H activity

Cleavage of the target mRNA by RNase H greatly enhances the inhibitory effects of antisense oligonucleotides. It is presently believed that the E. Coli RNase H requires only 3 to 4 unmodified residue binding site on the DNA portion of the DNA-RNA heteroduplex to elicit cleavage of the RNA. For this test an antisense oligonucleotide to 5LO mRNA (5-AAA TAG TGT TGC TGA TCT TGA C-3) having 6-aza T substituted for each T nucleotide was utilized for RNase H testing. In the test oligonucleotide the positions modified to contain 6-aza T were each separated by no more than two nature bases—thus the oligonucleotide should demonstrate recognition by E. Coli RNase H. A natural complementary DNA (5 AAA TAG TGT TGC TGA TCT TGA C-3) was synthesized for comparison. The 5-LO mRNA (2.5 kb) was synthesized in vitro. The natural DNA (AAA TAG TGT TGC TGA TCT TGA C) and the 6-aza T containing modified oligonucleotide (AAA TAG TGT TGC TGA TCT TGA C), both being antisense DNA to 5-LO mRNA, were synthesized by automated DNA synthesis. The mRNA was heated for 30 min at 60° C. in the presence of a 3 times molar excess of each of the natural and modified oligonucleotide, and with the natural oligonucleotide as a control. Following incubation, the solutions were slowly cooled to 37° C. and RNase H (E. Coli) was added. The RNase H treated solutions were allowed to stand at 37° C. for 30 min. The degradation products were analyzed by 1.2% agarose/formaldehyde electrophoresis and visualized with ethidium bromide for quantitation. The results indicated that RNase H (E. Coli) was able to recognize and cleave mRNA bound to either natural or modified DNA containing 6-aza T with equal effectiveness.

What is claimed is:

1. An oligonucleotide or an oligonucleotide analog comprising at least five covalently bound nucleoside units connected together by phosphate linkages, which nucleoside units individually comprise a ribose or deoxyribose sugar portion covalently bound to a base portion, wherein a plurality of base portions are pyrimidine bases; and at least one of said pyrimidine bases is a modified pyrimidine base having the structure:

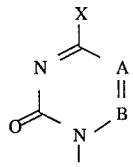

wherein:

X=OH or NH$_2$;

B is selected from the group consisting of:
C-lower alkyl, N, C—CF$_3$, C—F, C—Cl, C—Br, C—I, C-halocarbon, C—NO$_2$, C—CF$_3$, C—SH, C—SCH$_3$, C—OH, C—O-lower alkyl, C—CH$_2$OH, C—CH$_2$SH, C—CH$_2$SCH$_3$, C—CH$_2$OCH$_3$, C—NH$_2$, C—CH$_2$NH$_2$, C—alkyl-NH$_2$, C-benzyl, C-aryl, C-substituted aryl or benzyl wherein said substituents are selected from the group consisting of methyl, hydroxyl, alkoxy, alcohol, benzyl, phenyl, nitro, thiol, and halogen; provided that when B is N, then said sugar portion to which said modified pyrimidine base is bound is deoxyribose; and A is selected from the group consisting of:
C—H, N, C—CF$_3$, C-halocarbon, C—NO$_2$, C—OCF$_3$, C—SH, C—SCH$_3$, C—OH, C—O-lower alkyl, C—CH$_2$OH, C—CH$_2$SH, C—CH$_2$SCH$_3$, C—CH$_2$OCH$_3$, C—NH$_2$, C—CH$_2$NH$_2$, C-benzyl, C-aryl, C-substituted aryl or benzyl wherein said substituents are selected from the group consisting of methyl, hydroxyl, alkoxy, alcohol, benzyl, phenyl, nitro, thiol, and halogen.

2. The oligonucleotide or oligonucleotide analog of claim 1 wherein A is C—O-lower alkyl, C—OH, C-phenyl, C-benzyl, C—NO$_2$, C—SH, or C-halocarbon.

3. The oligonucleotide or oligonucleotide analog of claim 1 wherein B is C-lower alkyl, C—O-lower alkyl, C—OH, C-phenyl, C-benzyl, C—NO$_2$, C—SH, C-halocarbon, C—F, C—Cl, C—Br, or C—I.

4. The compound claim 1 wherein at least one of A and B is C-halocarbon or B is C-halogen.

5. The compound of claim 1 wherein at least one of A and B is nitrogen.

6. The oligonucleotide or oligonucleotide analog of claim 1 wherein at least one of A and B is C—CF$_3$ or B is C—CH$_3$.

7. The oligonucleotide or oligonucleotide analog of claim 1 wherein A is C—CF$_3$ and B is nitrogen.

8. The compound of claim 1 wherein said modified pyrimidine base is at a 3' or a 5' end of said compound.

9. The compound of claim 1 wherein said modified pyrimidine base is at a 3' end of said compound.

10. The compound of claim 1 wherein up to about 3 modified pyrimidine bases are incorporated at a 3' end of said compound.

11. The compound of claim 1 wherein at least about 1% of said pyrimidine bases are said modified pyrimidine bases.

12. The compound of claim 1 wherein at least about 10% of said pyrimidine bases are said modified pyrimidine bases.

13. The compound of claim 1 wherein at least about 25% of said pyrimidine bases are said modified pyrimidine bases.

14. The compound of claim 1 wherein at least about 50% of said pyrimidine bases are said modified pyrimidine bases.

15. The compound of claim 1 wherein substantially all of said pyrimidine bases are said modified pyrimidine bases.

16. The compound of claim 1 wherein the sugar moiety of the pyrimidine is ribose or deoxyribose.

17. The compound of claim 1 wherein said nucleoside units are bound with phosphorothioate, methyl phosphonate, or phosphate alkylate groups.

18. The compound of claim 1 which exhibits improved nuclease resistance as compared to corresponding wild type oligonucleotides.

* * * * *

UNITED STATES PATENT AND TRADEMARK OFFICE
CERTIFICATE OF CORRECTION

PATENT NO. : 5,614,617
DATED : March 25,1997
INVENTOR(S) : Phillip D. Cook et al It is certified that error appears in the above-identified patent and that said Letters Patent is hereby corrected as shown below:

Col. 2, line 29, "e" after will should be -be-.

Col. 4, line 23, "Of" should be -of-.

Col. 5, line 33, "Nucieic" should be --Nucleic--

Col. 8, line 12, "Imay" in the beginning of the line should be --may-.

Col. 13, line 11, "i" should be --1--.

Col. 21, line 28, after "used" insert a period --.--.

Col. 21, line 34, before "Autoradiogrphy" insert a period -.-.

Col. 21, line 46, "hy" should be ---by-

Col. 21, line 48, "quantirate" should be -quantitate-.

Col. 21, line 59, "hy" should be --by--.

UNITED STATES PATENT AND TRADEMARK OFFICE
CERTIFICATE OF CORRECTION

PATENT NO. : 5,614,617
DATED : March 25, 1997
INVENTOR(S) : Phillip D. Cook, et al It is certified that error appears in the above-identified patent and that said Letters Patent is hereby corrected as shown below:

Col. 85, line 24, "C-CF$_3$" should be -C-OCF$_3$-.

Signed and Sealed this

Sixth Day of October, 1998

Attest:

BRUCE LEHMAN

*Attesting Officer*   Commissioner of Patents and Trademarks

SEQUENCE LISTING ( 1 ) GENERAL INFORMATION:

( i i i ) NUMBER OF SEQUENCES: 65

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: Modified-site
        ( B ) LOCATION: 1
        ( D ) OTHER INFORMATION: 6-aza- thymidine substitution ( i x ) FEATURE:
        ( A ) NAME/KEY: Modified-site
        ( B ) LOCATION: 2
        ( D ) OTHER INFORMATION: 6-aza- thymidine substitution ( i x ) FEATURE:
        ( A ) NAME/KEY: Modified-site
        ( B ) LOCATION: 3
        ( D ) OTHER INFORMATION: 6-aza- thymidine substitution ( i x ) FEATURE:
        ( A ) NAME/KEY: Modified-site
        ( B ) LOCATION: 4
        ( D ) OTHER INFORMATION: 6-aza- thymidine substitution ( i x ) FEATURE:
        ( A ) NAME/KEY: Modified-site
        ( B ) LOCATION: 5
        ( D ) OTHER INFORMATION: 6-aza- thymidine substitution ( i x ) FEATURE:
        ( A ) NAME/KEY: Modified-site
        ( B ) LOCATION: 6
        ( D ) OTHER INFORMATION: 6-aza- thymidine substitution ( i x ) FEATURE:
        ( A ) NAME/KEY: Modified-site
        ( B ) LOCATION: 7
        ( D ) OTHER INFORMATION: 6-aza- thymidine substitution ( i x ) FEATURE:
        ( A ) NAME/KEY: Modified-site
        ( B ) LOCATION: 8
        ( D ) OTHER INFORMATION: 6-aza- thymidine substitution ( i x ) FEATURE:
        ( A ) NAME/KEY: Modified-site
        ( B ) LOCATION: 9
        ( D ) OTHER INFORMATION: 6-aza- thymidine substitution ( i x ) FEATURE:
        ( A ) NAME/KEY: Modified-site
        ( B ) LOCATION: 10
        ( D ) OTHER INFORMATION: 6-aza- thymidine substitution ( i x ) FEATURE:
        ( A ) NAME/KEY: Modified-site
        ( B ) LOCATION: 11
        ( D ) OTHER INFORMATION: 6-aza- thymidine substitution ( i x ) FEATURE:
        ( A ) NAME/KEY: Modified-site
        ( B ) LOCATION: 12
        ( D ) OTHER INFORMATION: 6-aza- thymidine substitution ( i x ) FEATURE:
        ( A ) NAME/KEY: Modified-site (B) LOCATION: 13
(D) OTHER INFORMATION: 6-aza- thymidine substitution (ix) FEATURE:
(A) NAME/KEY: Modified-site
(B) LOCATION: 14
(D) OTHER INFORMATION: 6-aza- thymidine substitution (xi) SEQUENCE DESCRIPTION: SEQ ID NO:1:

TTTTTTTTTT TTTTT                                                                15

(2) INFORMATION FOR SEQ ID NO:2:

(i) SEQUENCE CHARACTERISTICS:
(A) LENGTH: 16 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: Modified-site
(B) LOCATION: 2
(D) OTHER INFORMATION: 6-aza- thymidine substitution (ix) FEATURE:
(A) NAME/KEY: Modified-site
(B) LOCATION: 4
(D) OTHER INFORMATION: 6-aza- thymidine substitution (ix) FEATURE:
(A) NAME/KEY: Modified-site
(B) LOCATION: 6
(D) OTHER INFORMATION: 6-aza- thymidine substitution (ix) FEATURE:
(A) NAME/KEY: Modified-site
(B) LOCATION: 8
(D) OTHER INFORMATION: 6-aza- thymidine substitution (ix) FEATURE:
(A) NAME/KEY: Modified-site
(B) LOCATION: 10
(D) OTHER INFORMATION: 6-aza- thymidine substitution (ix) FEATURE:
(A) NAME/KEY: Modified-site
(B) LOCATION: 12
(D) OTHER INFORMATION: 6-aza- thymidine substitution (ix) FEATURE:
(A) NAME/KEY: Modified-site
(B) LOCATION: 14
(D) OTHER INFORMATION: 6-aza- thymidine substitution (xi) SEQUENCE DESCRIPTION: SEQ ID NO:2:

ATATATATAT ATATAT                                                               16

(2) INFORMATION FOR SEQ ID NO:3:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: Modified-site
(B) LOCATION: 1
(D) OTHER INFORMATION: 6-aza- thymidine substitution (ix) FEATURE:
(A) NAME/KEY: Modified-site ( B ) LOCATION: 7
                ( D ) OTHER INFORMATION: 6-aza- thymidine substitution ( i x ) FEATURE:
                ( A ) NAME/KEY: Modified-site
                ( B ) LOCATION: 9
                ( D ) OTHER INFORMATION: 6-aza- thymidine substitution ( x i ) SEQUENCE DESCRIPTION: SEQ ID NO:3:

TCCAGGTGTC CGCAT                                                                                    15

( 2 ) INFORMATION FOR SEQ ID NO:4:

( i ) SEQUENCE CHARACTERISTICS:
                ( A ) LENGTH: 16 base pairs
                ( B ) TYPE: nucleic acid
                ( C ) STRANDEDNESS: single
                ( D ) TOPOLOGY: linear ( i i ) MOLECULE TYPE: DNA (genomic)

( i x ) FEATURE:
                ( A ) NAME/KEY: Modified-site
                ( B ) LOCATION: 1
                ( D ) OTHER INFORMATION: 6-aza- thymidine substitution ( i x ) FEATURE:
                ( A ) NAME/KEY: Modified-site
                ( B ) LOCATION: 7
                ( D ) OTHER INFORMATION: 6-aza- thymidine substitution ( i x ) FEATURE:
                ( A ) NAME/KEY: Modified-site
                ( B ) LOCATION: 9
                ( D ) OTHER INFORMATION: 6-aza- thymidine substitution ( i x ) FEATURE:
                ( A ) NAME/KEY: Modified-site
                ( B ) LOCATION: 15
                ( D ) OTHER INFORMATION: 6-aza- thymidine substitution ( x i ) SEQUENCE DESCRIPTION: SEQ ID NO:4:

TCCAGGTGTC CGCATC                                                                                   16

( 2 ) INFORMATION FOR SEQ ID NO:5:

( i ) SEQUENCE CHARACTERISTICS:
                ( A ) LENGTH: 16 base pairs
                ( B ) TYPE: nucleic acid
                ( C ) STRANDEDNESS: single
                ( D ) TOPOLOGY: linear ( i i ) MOLECULE TYPE: DNA (genomic)

( i x ) FEATURE:
                ( A ) NAME/KEY: Modified-site
                ( B ) LOCATION: 1
                ( D ) OTHER INFORMATION: 6-aza- thymidine substitution ( i x ) FEATURE:
                ( A ) NAME/KEY: Modified-site
                ( B ) LOCATION: 15
                ( D ) OTHER INFORMATION: 6-aza- thymidine substitution ( x i ) SEQUENCE DESCRIPTION: SEQ ID NO:5:

TCCAGGTGTC CGCATC                                                                                   16

( 2 ) INFORMATION FOR SEQ ID NO:6:

( i ) SEQUENCE CHARACTERISTICS:
                ( A ) LENGTH: 16 base pairs
                ( B ) TYPE: nucleic acid
                ( C ) STRANDEDNESS: single
                ( D ) TOPOLOGY: linear ( i i ) MOLECULE TYPE: DNA (genomic)

( i x ) FEATURE:
                ( A ) NAME/KEY: Modified-site
                ( B ) LOCATION: 15
                ( D ) OTHER INFORMATION: 6-aza- thymidine substitution ( x i ) SEQUENCE DESCRIPTION: SEQ ID NO:6:

TCCAGGTGTC CGCATC 16

( 2 ) INFORMATION FOR SEQ ID NO:7:

( i ) SEQUENCE CHARACTERISTICS:
                ( A ) LENGTH: 16 base pairs
                ( B ) TYPE: nucleic acid
                ( C ) STRANDEDNESS: single
                ( D ) TOPOLOGY: linear ( i i ) MOLECULE TYPE: DNA (genomic)

( i x ) FEATURE:
                ( A ) NAME/KEY: Modified-site
                ( B ) LOCATION: 1
                ( D ) OTHER INFORMATION: 6-aza- thymidine substitution ( x i ) SEQUENCE DESCRIPTION: SEQ ID NO:7:

TCCAGGTGTC CGCATC 16

( 2 ) INFORMATION FOR SEQ ID NO:8:

( i ) SEQUENCE CHARACTERISTICS:
                ( A ) LENGTH: 16 base pairs
                ( B ) TYPE: nucleic acid
                ( C ) STRANDEDNESS: single
                ( D ) TOPOLOGY: linear ( i i ) MOLECULE TYPE: DNA (genomic)

( i x ) FEATURE:
                ( A ) NAME/KEY: Modified-site
                ( B ) LOCATION: 1
                ( D ) OTHER INFORMATION: 6-aza- thymidine substitution ( i x ) FEATURE:
                ( A ) NAME/KEY: Modified-site
                ( B ) LOCATION: 7
                ( D ) OTHER INFORMATION: 6-aza- thymidine substitution ( x i ) SEQUENCE DESCRIPTION: SEQ ID NO:8:

TCCAGGTGTC CGCATC 16

( 2 ) INFORMATION FOR SEQ ID NO:9:

( i ) SEQUENCE CHARACTERISTICS:
                ( A ) LENGTH: 16 base pairs
                ( B ) TYPE: nucleic acid
                ( C ) STRANDEDNESS: single
                ( D ) TOPOLOGY: linear ( i i ) MOLECULE TYPE: DNA (genomic)

( i x ) FEATURE:
                ( A ) NAME/KEY: Modified-site
                ( B ) LOCATION: 9
                ( D ) OTHER INFORMATION: 6-aza- thymidine substitution ( i x ) FEATURE:
                ( A ) NAME/KEY: Modified-site
                ( B ) LOCATION: 9
                ( D ) OTHER INFORMATION: 6-aza- thymidine substitution ( x i ) SEQUENCE DESCRIPTION: SEQ ID NO:9:

TCCAGGTGTC CGCATC                                                                      16

( 2 ) INFORMATION FOR SEQ ID NO:10:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: Modified-site
        ( B ) LOCATION: 1
        ( D ) OTHER INFORMATION: 6-aza- thymidine substitution ( i x ) FEATURE:
        ( A ) NAME/KEY: Modified-site
        ( B ) LOCATION: 7
        ( D ) OTHER INFORMATION: 6-aza- thymidine substitution ( i x ) FEATURE:
        ( A ) NAME/KEY: Modified-site
        ( B ) LOCATION: 9
        ( D ) OTHER INFORMATION: 6-aza- thymidine substitution ( i x ) FEATURE:
        ( A ) NAME/KEY: Modified-site
        ( B ) LOCATION: 13
        ( D ) OTHER INFORMATION: 6-aza- thymidine substitution ( i x ) FEATURE:
        ( A ) NAME/KEY: Modified-site
        ( B ) LOCATION: 14
        ( D ) OTHER INFORMATION: 6-aza- thymidine substitution ( i x ) FEATURE:
        ( A ) NAME/KEY: Modified-site
        ( B ) LOCATION: 15
        ( D ) OTHER INFORMATION: 6-aza- thymidine substitution ( x i ) SEQUENCE DESCRIPTION: SEQ ID NO:10:

TCCAGGTGTC CGTTTC                                                                      16

( 2 ) INFORMATION FOR SEQ ID NO:11:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: Modified-site
        ( B ) LOCATION: 1
        ( D ) OTHER INFORMATION: 6-aza- thymidine substitution ( i x ) FEATURE:
        ( A ) NAME/KEY: Modified-site
        ( B ) LOCATION: 7
        ( D ) OTHER INFORMATION: 6-aza- thymidine substitution ( i x ) FEATURE:
        ( A ) NAME/KEY: Modified-site
        ( B ) LOCATION: 9
        ( D ) OTHER INFORMATION: 6-aza- thymidine substitution ( i x ) FEATURE:
        ( A ) NAME/KEY: Modified-site
        ( B ) LOCATION: 13
        ( D ) OTHER INFORMATION: 6-aza- thymidine substitution;
            P of the phosphodiester bond is
            replaced by an S (ix) FEATURE:
    (A) NAME/KEY: Modified-site
    (B) LOCATION: 14
    (D) OTHER INFORMATION: 6-aza- thymidine substitution;
        P of the phosphodiester bond is
        replaced by an S (ix) FEATURE:
    (A) NAME/KEY: Modified-site
    (B) LOCATION: 15
    (D) OTHER INFORMATION: 6-aza- thymidine substitution;
        P of the phosphodiester bond is
        replaced by an S (xi) SEQUENCE DESCRIPTION: SEQ ID NO:11:

TCCAGGTGTC CGTTTC    16

(2) INFORMATION FOR SEQ ID NO:12:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: Modified-site
        (B) LOCATION: 5
        (D) OTHER INFORMATION: 6-aza- thymidine substitution (ix) FEATURE:
        (A) NAME/KEY: Modified-site
        (B) LOCATION: 7
        (D) OTHER INFORMATION: 6-aza- thymidine substitution (ix) FEATURE:
        (A) NAME/KEY: Modified-site
        (B) LOCATION: 13
        (D) OTHER INFORMATION: 6-aza- thymidine substitution (xi) SEQUENCE DESCRIPTION: SEQ ID NO:12:

CGACTATGCA AGTAC    15

(2) INFORMATION FOR SEQ ID NO:13:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: Modified-site
        (B) LOCATION: 12
        (D) OTHER INFORMATION: 6-aza- thymidine substitution (ix) FEATURE:
        (A) NAME/KEY: Modified-site
        (B) LOCATION: 13
        (D) OTHER INFORMATION: 6-aza- thymidine substitution (ix) FEATURE:
        (A) NAME/KEY: Modified-site
        (B) LOCATION: 14
        (D) OTHER INFORMATION: 6-aza- thymidine substitution (xi) SEQUENCE DESCRIPTION: SEQ ID NO:13:

CGACTATGCA ATTTC    15

(2) INFORMATION FOR SEQ ID NO:14:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: Modified-site
  ( B ) LOCATION: 1
  ( D ) OTHER INFORMATION: 6-aza- thymidine substitution ( i x ) FEATURE:
  ( A ) NAME/KEY: Modified-site
  ( B ) LOCATION: 2
  ( D ) OTHER INFORMATION: 6-aza- thymidine substitution ( i x ) FEATURE:
  ( A ) NAME/KEY: Modified-site
  ( B ) LOCATION: 3
  ( D ) OTHER INFORMATION: 6-aza- thymidine substitution ( x i ) SEQUENCE DESCRIPTION: SEQ ID NO:14:

TTTCTATGCA AGTAC                                                                                   15

( 2 ) INFORMATION FOR SEQ ID NO:15:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: Modified-site
    ( B ) LOCATION: 2
    ( D ) OTHER INFORMATION: 6-aza- thymidine substitution ( i x ) FEATURE:
    ( A ) NAME/KEY: Modified-site
    ( B ) LOCATION: 6
    ( D ) OTHER INFORMATION: 6-aza- thymidine substitution ( i x ) FEATURE:
    ( A ) NAME/KEY: Modified-site
    ( B ) LOCATION: 8
    ( D ) OTHER INFORMATION: 6-aza- thymidine substitution ( i x ) FEATURE:
    ( A ) NAME/KEY: Modified-site
    ( B ) LOCATION: 11
    ( D ) OTHER INFORMATION: 6-aza- thymidine substitution ( x i ) SEQUENCE DESCRIPTION: SEQ ID NO:15:

GTCCATGTCG TACGC                                                                                   15

( 2 ) INFORMATION FOR SEQ ID NO:16:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: Modified-site
    ( B ) LOCATION: 8
    ( D ) OTHER INFORMATION: 6-aza- thymidine substitution ( i x ) FEATURE:

(A) NAME/KEY: Modified-site
                (B) LOCATION: 12
                (D) OTHER INFORMATION: 6-aza- thymidine substitution (ix) FEATURE:
                (A) NAME/KEY: Modified-site
                (B) LOCATION: 14
                (D) OTHER INFORMATION: 6-aza- thymidine substitution (ix) FEATURE:
                (A) NAME/KEY: Modified-site
                (B) LOCATION: 17
                (D) OTHER INFORMATION: 6-aza- thymidine substitution (xi) SEQUENCE DESCRIPTION: SEQ ID NO:16:

ACCGAGGTCC ATGTCGTACG C 21

(2) INFORMATION FOR SEQ ID NO:17:

(i) SEQUENCE CHARACTERISTICS:
                (A) LENGTH: 21 base pairs
                (B) TYPE: nucleic acid
                (C) STRANDEDNESS: single
                (D) TOPOLOGY: linear (ii) MOLECULE TYPE: DNA (genomic)

(ix) FEATURE:
                (A) NAME/KEY: Modified-site
                (B) LOCATION: 2
                (D) OTHER INFORMATION: 6-aza- cytidine substitution (ix) FEATURE:
                (A) NAME/KEY: Modified-site
                (B) LOCATION: 3
                (D) OTHER INFORMATION: 6-aza- cytidine substitution (ix) FEATURE:
                (A) NAME/KEY: Modified-site
                (B) LOCATION: 8
                (D) OTHER INFORMATION: 6-aza- thymidine substitution (ix) FEATURE:
                (A) NAME/KEY: Modified-site
                (B) LOCATION: 9
                (D) OTHER INFORMATION: 6-aza- cytidine substitution (ix) FEATURE:
                (A) NAME/KEY: Modified-site
                (B) LOCATION: 10
                (D) OTHER INFORMATION: 6-aza- cytidine substitution (ix) FEATURE:
                (A) NAME/KEY: Modified-site
                (B) LOCATION: 12
                (D) OTHER INFORMATION: 6-aza- thymidine substitution (ix) FEATURE:
                (A) NAME/KEY: Modified-site
                (B) LOCATION: 14
                (D) OTHER INFORMATION: 6-aza- thymidine substitution (ix) FEATURE:
                (A) NAME/KEY: Modified-site
                (B) LOCATION: 15
                (D) OTHER INFORMATION: 6-aza- cytidine substitution (ix) FEATURE:
                (A) NAME/KEY: Modified-site
                (B) LOCATION: 17
                (D) OTHER INFORMATION: 6-aza- thymidine substitution (ix) FEATURE:
                (A) NAME/KEY: Modified-site
                (B) LOCATION: 19
                (D) OTHER INFORMATION: 6-aza- cytidine substitution (xi) SEQUENCE DESCRIPTION: SEQ ID NO:17:

ACCGAGGTCC ATGTCGTACG C    21

( 2 ) INFORMATION FOR SEQ ID NO:18:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: Modified-site
        ( B ) LOCATION: 3
        ( D ) OTHER INFORMATION: 6-aza- thymidine substitution ( i x ) FEATURE:
        ( A ) NAME/KEY: Modified-site
        ( B ) LOCATION: 4
        ( D ) OTHER INFORMATION: 6-aza- thymidine substitution ( i x ) FEATURE:
        ( A ) NAME/KEY: Modified-site
        ( B ) LOCATION: 9
        ( D ) OTHER INFORMATION: 6-aza- thymidine substitution ( x i ) SEQUENCE DESCRIPTION: SEQ ID NO:18:

CCTTCCCCTC    10

( 2 ) INFORMATION FOR SEQ ID NO:19:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: Modified-site
        ( B ) LOCATION: 1
        ( D ) OTHER INFORMATION: 6-aza- cytidine substitution ( i x ) FEATURE:
        ( A ) NAME/KEY: Modified-site
        ( B ) LOCATION: 2
        ( D ) OTHER INFORMATION: 6-aza- cytidine substitution ( i x ) FEATURE:
        ( A ) NAME/KEY: Modified-site
        ( B ) LOCATION: 3
        ( D ) OTHER INFORMATION: 6-aza- cytidine substitution ( i x ) FEATURE:
        ( A ) NAME/KEY: Modified-site
        ( B ) LOCATION: 4
        ( D ) OTHER INFORMATION: 6-aza- cytidine substitution ( i x ) FEATURE:
        ( A ) NAME/KEY: Modified-site
        ( B ) LOCATION: 5
        ( D ) OTHER INFORMATION: 6-aza- cytidine substitution ( i x ) FEATURE:
        ( A ) NAME/KEY: Modified-site
        ( B ) LOCATION: 6
        ( D ) OTHER INFORMATION: 6-aza- cytidine substitution ( i x ) FEATURE:
        ( A ) NAME/KEY: Modified-site
        ( B ) LOCATION: 7
        ( D ) OTHER INFORMATION: 6-aza- cytidine substitution ( i x ) FEATURE:

(A) NAME/KEY: Modified-site
        (B) LOCATION: 8
        (D) OTHER INFORMATION: 6-aza- cytidine substitution (ix) FEATURE:
        (A) NAME/KEY: Modified-site
        (B) LOCATION: 9
        (D) OTHER INFORMATION: 6-aza- cytidine substitution (ix) FEATURE:
        (A) NAME/KEY: Modified-site
        (B) LOCATION: 10
        (D) OTHER INFORMATION: 6-aza- cytidine substitution (ix) FEATURE:
        (A) NAME/KEY: Modified-site
        (B) LOCATION: 11
        (D) OTHER INFORMATION: 6-aza- cytidine substitution (ix) FEATURE:
        (A) NAME/KEY: Modified-site
        (B) LOCATION: 12
        (D) OTHER INFORMATION: 6-aza- cytidine substitution (ix) FEATURE:
        (A) NAME/KEY: Modified-site
        (B) LOCATION: 13
        (D) OTHER INFORMATION: 6-aza- cytidine substitution (ix) FEATURE:
        (A) NAME/KEY: Modified-site
        (B) LOCATION: 14
        (D) OTHER INFORMATION: 6-aza- cytidine substitution (xi) SEQUENCE DESCRIPTION: SEQ ID NO:19:

CCCCCCCCC CCCC                                                                                    15

(2) INFORMATION FOR SEQ ID NO:20:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: Modified-site
        (B) LOCATION: 1
        (D) OTHER INFORMATION: 6-aza- cytidine substitution (ix) FEATURE:
        (A) NAME/KEY: Modified-site
        (B) LOCATION: 2
        (D) OTHER INFORMATION: 6-aza- cytidine substitution (ix) FEATURE:
        (A) NAME/KEY: Modified-site
        (B) LOCATION: 3
        (D) OTHER INFORMATION: 6-aza- cytidine substitution (xi) SEQUENCE DESCRIPTION: SEQ ID NO:20:

CCCAGGTGTC CGCATC                                                                                 16

(2) INFORMATION FOR SEQ ID NO:21:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(ix) FEATURE:

(A) NAME/KEY: Modified-site
                    (B) LOCATION: 10
                    (D) OTHER INFORMATION: 6-aza- cytidine substitution (ix) FEATURE:
                    (A) NAME/KEY: Modified-site
                    (B) LOCATION: 11
                    (D) OTHER INFORMATION: 6-aza- cytidine substitution (xi) SEQUENCE DESCRIPTION: SEQ ID NO:21:

TCCAGGTGTC CGCATC                                                                                      16

(2) INFORMATION FOR SEQ ID NO:22:

(i) SEQUENCE CHARACTERISTICS:
                    (A) LENGTH: 16 base pairs
                    (B) TYPE: nucleic acid
                    (C) STRANDEDNESS: single
                    (D) TOPOLOGY: linear (ii) MOLECULE TYPE: DNA (genomic)

(ix) FEATURE:
                    (A) NAME/KEY: Modified-site
                    (B) LOCATION: 13
                    (D) OTHER INFORMATION: 6-aza- cytidine substitution (ix) FEATURE:
                    (A) NAME/KEY: Modified-site
                    (B) LOCATION: 14
                    (D) OTHER INFORMATION: 6-aza- cytidine substitution (ix) FEATURE:
                    (A) NAME/KEY: Modified-site
                    (B) LOCATION: 15
                    (D) OTHER INFORMATION: 6-aza- cytidine substitution (xi) SEQUENCE DESCRIPTION: SEQ ID NO:22:

TCCAGGTGTC CGCCCC                                                                                      16

(2) INFORMATION FOR SEQ ID NO:23:

(i) SEQUENCE CHARACTERISTICS:
                    (A) LENGTH: 16 base pairs
                    (B) TYPE: nucleic acid
                    (C) STRANDEDNESS: single
                    (D) TOPOLOGY: linear (ii) MOLECULE TYPE: DNA (genomic)

(ix) FEATURE:
                    (A) NAME/KEY: Modified-site
                    (B) LOCATION: 14
                    (D) OTHER INFORMATION: 6-aza- cytidine substitution (ix) FEATURE:
                    (A) NAME/KEY: Modified-site
                    (B) LOCATION: 15
                    (D) OTHER INFORMATION: 6-aza- cytidine substitution (xi) SEQUENCE DESCRIPTION: SEQ ID NO:23:

TCCAGGTGTC CGCCCC                                                                                      16

(2) INFORMATION FOR SEQ ID NO:24:

(i) SEQUENCE CHARACTERISTICS:
                    (A) LENGTH: 15 base pairs
                    (B) TYPE: nucleic acid
                    (C) STRANDEDNESS: single
                    (D) TOPOLOGY: linear (ii) MOLECULE TYPE: DNA (genomic)

(ix) FEATURE:

( A ) NAME/KEY: Modified-site
            ( B ) LOCATION: 12
            ( D ) OTHER INFORMATION: 6-aza- cytidine substitution ( i x ) FEATURE:
            ( A ) NAME/KEY: Modified-site
            ( B ) LOCATION: 13
            ( D ) OTHER INFORMATION: 6-aza- cytidine substitution ( i x ) FEATURE:
            ( A ) NAME/KEY: Modified-site
            ( B ) LOCATION: 14
            ( D ) OTHER INFORMATION: 6-aza- cytidine substitution ( x i ) SEQUENCE DESCRIPTION: SEQ ID NO:24:

CGACTATGCA ACCCC                    15

( 2 ) INFORMATION FOR SEQ ID NO:25:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( i i ) MOLECULE TYPE: DNA (genomic)

( i x ) FEATURE:
            ( A ) NAME/KEY: Modified-site
            ( B ) LOCATION: 1
            ( D ) OTHER INFORMATION: 6-aza- cytidine substitution ( i x ) FEATURE:
            ( A ) NAME/KEY: Modified-site
            ( B ) LOCATION: 2
            ( D ) OTHER INFORMATION: 6-aza- cytidine substitution ( i x ) FEATURE:
            ( A ) NAME/KEY: Modified-site
            ( B ) LOCATION: 3
            ( D ) OTHER INFORMATION: 6-aza- cytidine substitution ( x i ) SEQUENCE DESCRIPTION: SEQ ID NO:25:

CCCCTATGCA AGTAC                    15

( 2 ) INFORMATION FOR SEQ ID NO:26:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( i i ) MOLECULE TYPE: DNA (genomic)

( i x ) FEATURE:
            ( A ) NAME/KEY: Modified-site
            ( B ) LOCATION: 1
            ( D ) OTHER INFORMATION: 6-aza- cytidine substitution ( i x ) FEATURE:
            ( A ) NAME/KEY: Modified-site
            ( B ) LOCATION: 4
            ( D ) OTHER INFORMATION: 6-aza- cytidine substitution ( i x ) FEATURE:
            ( A ) NAME/KEY: Modified-site
            ( B ) LOCATION: 9
            ( D ) OTHER INFORMATION: 6-aza- cytidine substitution ( x i ) SEQUENCE DESCRIPTION: SEQ ID NO:26:

CGACTATGCA AGTAC                    15

( 2 ) INFORMATION FOR SEQ ID NO:27:

( i ) SEQUENCE CHARACTERISTICS:
   ( A ) LENGTH: 21 base pairs
   ( B ) TYPE: nucleic acid
   ( C ) STRANDEDNESS: single
   ( D ) TOPOLOGY: linear ( i i ) MOLECULE TYPE: DNA (genomic)

( i x ) FEATURE:
   ( A ) NAME/KEY: Modified-site
   ( B ) LOCATION: 2
   ( D ) OTHER INFORMATION: 6-aza- cytidine substitution ( i x ) FEATURE:
   ( A ) NAME/KEY: Modified-site
   ( B ) LOCATION: 3
   ( D ) OTHER INFORMATION: 6-aza- cytidine substitution ( i x ) FEATURE:
   ( A ) NAME/KEY: Modified-site
   ( B ) LOCATION: 9
   ( D ) OTHER INFORMATION: 6-aza- cytidine substitution ( i x ) FEATURE:
   ( A ) NAME/KEY: Modified-site
   ( B ) LOCATION: 10
   ( D ) OTHER INFORMATION: 6-aza- cytidine substitution ( i x ) FEATURE:
   ( A ) NAME/KEY: Modified-site
   ( B ) LOCATION: 15
   ( D ) OTHER INFORMATION: 6-aza- cytidine substitution ( i x ) FEATURE:
   ( A ) NAME/KEY: Modified-site
   ( B ) LOCATION: 19
   ( D ) OTHER INFORMATION: 6-aza- cytidine substitution ( x i ) SEQUENCE DESCRIPTION: SEQ ID NO:27:

ACCGAGGTCC ATGTCGTACG C                                          21

( 2 ) INFORMATION FOR SEQ ID NO:28:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: Modified-site
      ( B ) LOCATION: 1
      ( D ) OTHER INFORMATION: 5- trifluoromethyl-2'-
            deoxyuridine substitution ( x i ) SEQUENCE DESCRIPTION: SEQ ID NO:28:

TCCAGGTGTC CGCATC                                                16

( 2 ) INFORMATION FOR SEQ ID NO:29:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: Modified-site
      ( B ) LOCATION: 1
      ( D ) OTHER INFORMATION: 5- trifluoromethyl-2'-
            deoxyuridine substitution ( i x ) FEATURE:
        ( A ) NAME/KEY: Modified-site
        ( B ) LOCATION: 7
        ( D ) OTHER INFORMATION: 5- trifluoromethyl-2'-
            deoxyuridine substitution ( x i ) SEQUENCE DESCRIPTION: SEQ ID NO:29:

TCCAGGTGTC CGCATC                                                                                              16

( 2 ) INFORMATION FOR SEQ ID NO:30:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: Modified-site
        ( B ) LOCATION: 1
        ( D ) OTHER INFORMATION: 5- trifluoromethyl-2'-
            deoxyuridine substitution ( i x ) FEATURE:
        ( A ) NAME/KEY: Modified-site
        ( B ) LOCATION: 7
        ( D ) OTHER INFORMATION: 5- trifluoromethyl-2'-
            deoxyuridine substitution ( i x ) FEATURE:
        ( A ) NAME/KEY: Modified-site
        ( B ) LOCATION: 9
        ( D ) OTHER INFORMATION: 5- trifluoromethyl-2'-
            deoxyuridine substitution ( x i ) SEQUENCE DESCRIPTION: SEQ ID NO:30:

TCCAGGTGTC CGCATC                                                                                             16

( 2 ) INFORMATION FOR SEQ ID NO:31:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: Modified-site
        ( B ) LOCATION: 7
        ( D ) OTHER INFORMATION: 5- trifluoromethyl-2'-
            deoxyuridine substitution ( i x ) FEATURE:
        ( A ) NAME/KEY: Modified-site
        ( B ) LOCATION: 9
        ( D ) OTHER INFORMATION: 5- trifluoromethyl-2'-
            deoxyuridine substitution ( x i ) SEQUENCE DESCRIPTION: SEQ ID NO:31:

TCCAGGTGTC CGCATC                                                                                              16

( 2 ) INFORMATION FOR SEQ ID NO:32:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
    ( A ) NAME/KEY: Modified-site
    ( B ) LOCATION: 15
    ( D ) OTHER INFORMATION: 5- trifluoromethyl-2'-
        deoxyuridine substitution ( x i ) SEQUENCE DESCRIPTION: SEQ ID NO:32:

TCCAGGTGTC CGCATC                                                                          16

( 2 ) INFORMATION FOR SEQ ID NO:33:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: Modified-site
    ( B ) LOCATION: 12
    ( D ) OTHER INFORMATION: 5- trifluoromethyl-2'-
        deoxyuridine substitution ( i x ) FEATURE:
    ( A ) NAME/KEY: Modified-site
    ( B ) LOCATION: 13
    ( D ) OTHER INFORMATION: 5- trifluoromethyl-2'-
        deoxyuridine substitution ( i x ) FEATURE:
    ( A ) NAME/KEY: Modified-site
    ( B ) LOCATION: 14
    ( D ) OTHER INFORMATION: 5- trifluoromethyl-2'-
        deoxyuridine substitution ( x i ) SEQUENCE DESCRIPTION: SEQ ID NO:33:

CGACTATGCA ATTTC                                                                      15

( 2 ) INFORMATION FOR SEQ ID NO:34:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: Modified-site
    ( B ) LOCATION: 1
    ( D ) OTHER INFORMATION: 5- trifluoromethyl-2'-
        deoxyuridine substitution ( i x ) FEATURE:
    ( A ) NAME/KEY: Modified-site
    ( B ) LOCATION: 2
    ( D ) OTHER INFORMATION: 5- trifluoromethyl-2'-
        deoxyuridine substitution ( i x ) FEATURE:
    ( A ) NAME/KEY: Modified-site
    ( B ) LOCATION: 3
    ( D ) OTHER INFORMATION: 5- trifluoromethyl-2'-
        deoxyuridine substitution ( x i ) SEQUENCE DESCRIPTION: SEQ ID NO:34:

TTTCTATGCA AGTAC                                                                      15

( 2 ) INFORMATION FOR SEQ ID NO:35:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: Modified-site
    ( B ) LOCATION: 8
    ( D ) OTHER INFORMATION: 5- trifluoromethyl-2'-
        deoxyuridine substitution ( i x ) FEATURE:
    ( A ) NAME/KEY: Modified-site
    ( B ) LOCATION: 12
    ( D ) OTHER INFORMATION: 5- trifluoromethyl-2'-
        deoxyuridine substitution ( i x ) FEATURE:
    ( A ) NAME/KEY: Modified-site
    ( B ) LOCATION: 14
    ( D ) OTHER INFORMATION: 5- trifluoromethyl-2'-
        deoxyuridine substitution ( i x ) FEATURE:
    ( A ) NAME/KEY: Modified-site
    ( B ) LOCATION: 17
    ( D ) OTHER INFORMATION: 5- trifluoromethyl-2'-
        deoxyuridine substitution ( x i ) SEQUENCE DESCRIPTION: SEQ ID NO:35:

ACCGAGGTCC ATGTCGTACG C                                              21

( 2 ) INFORMATION FOR SEQ ID NO:36:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: Modified-site
        ( B ) LOCATION: 1
        ( D ) OTHER INFORMATION: 5-fluoro-2'- deoxyuridine
            substitution ( i x ) FEATURE:
        ( A ) NAME/KEY: Modified-site
        ( B ) LOCATION: 2
        ( D ) OTHER INFORMATION: 5-fluoro-2'- deoxyuridine
            substitution ( i x ) FEATURE:
        ( A ) NAME/KEY: Modified-site
        ( B ) LOCATION: 3
        ( D ) OTHER INFORMATION: 5-fluoro-2'- deoxyuridine
            substitution ( i x ) FEATURE:
        ( A ) NAME/KEY: Modified-site
        ( B ) LOCATION: 4
        ( D ) OTHER INFORMATION: 5-fluoro-2'- deoxyuridine
            substitution ( i x ) FEATURE:
        ( A ) NAME/KEY: Modified-site
        ( B ) LOCATION: 5
        ( D ) OTHER INFORMATION: 5-fluoro-2'- deoxyuridine
            substitution ( i x ) FEATURE:
        ( A ) NAME/KEY: Modified-site ( B ) LOCATION: 6
                    ( D ) OTHER INFORMATION: 5-fluoro-2'- deoxyuridine
                            substitution ( i x ) FEATURE:
                    ( A ) NAME/KEY: Modified-site
                    ( B ) LOCATION: 7
                    ( D ) OTHER INFORMATION: 5-fluoro-2'- deoxyuridine
                            substitution ( i x ) FEATURE:
                    ( A ) NAME/KEY: Modified-site
                    ( B ) LOCATION: 8
                    ( D ) OTHER INFORMATION: 5-fluoro-2'- deoxyuridine
                            substitution ( i x ) FEATURE:
                    ( A ) NAME/KEY: Modified-site
                    ( B ) LOCATION: 9
                    ( D ) OTHER INFORMATION: 5-fluoro-2'- deoxyuridine
                            substitution ( i x ) FEATURE:
                    ( A ) NAME/KEY: Modified-site
                    ( B ) LOCATION: 10
                    ( D ) OTHER INFORMATION: 5-fluoro-2'- deoxyuridine
                            substitution ( i x ) FEATURE:
                    ( A ) NAME/KEY: Modified-site
                    ( B ) LOCATION: 11
                    ( D ) OTHER INFORMATION: 5-fluoro-2'- deoxyuridine
                            substitution ( i x ) FEATURE:
                    ( A ) NAME/KEY: Modified-site
                    ( B ) LOCATION: 12
                    ( D ) OTHER INFORMATION: 5-fluoro-2'- deoxyuridine
                            substitution ( i x ) FEATURE:
                    ( A ) NAME/KEY: Modified-site
                    ( B ) LOCATION: 13
                    ( D ) OTHER INFORMATION: 5-fluoro-2'- deoxyuridine
                            substitution ( i x ) FEATURE:
                    ( A ) NAME/KEY: Modified-site
                    ( B ) LOCATION: 14
                    ( D ) OTHER INFORMATION: 5-fluoro-2'- deoxyuridine
                            substitution ( i x ) FEATURE:
                    ( A ) NAME/KEY: Modified-site
                    ( B ) LOCATION: 15
                    ( D ) OTHER INFORMATION: 5-fluoro-2'- deoxyuridine
                            substitution ( x i ) SEQUENCE DESCRIPTION: SEQ ID NO:36:

TTTTTTTTTT TTTTTT                                                                                                           1 6

( 2 ) INFORMATION FOR SEQ ID NO:37:

( i ) SEQUENCE CHARACTERISTICS:
                    ( A ) LENGTH: 16 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i x ) FEATURE:
                    ( A ) NAME/KEY: Modified-site
                    ( B ) LOCATION: 15
                    ( D ) OTHER INFORMATION: 5-fluoro-2'- deoxyuridine
                            substitution ( x i ) SEQUENCE DESCRIPTION: SEQ ID NO:37:

TCCAGGTGTC CGCATC                    16

( 2 ) INFORMATION FOR SEQ ID NO:38:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: Modified-site
        ( B ) LOCATION: 7
        ( D ) OTHER INFORMATION: 5-fluoro-2'- deoxyuridine substitution ( i x ) FEATURE:
        ( A ) NAME/KEY: Modified-site
        ( B ) LOCATION: 9
        ( D ) OTHER INFORMATION: 5-fluoro-2'- deoxyuridine substitution ( x i ) SEQUENCE DESCRIPTION: SEQ ID NO:38:

TCCAGGTGTC CGCATC                    16

( 2 ) INFORMATION FOR SEQ ID NO:39:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: Modified-site
        ( B ) LOCATION: 1
        ( D ) OTHER INFORMATION: 5-fluoro-2'- deoxyuridine substitution ( x i ) SEQUENCE DESCRIPTION: SEQ ID NO:39:

TCCAGGTGTC CGCATC                    16

( 2 ) INFORMATION FOR SEQ ID NO:40:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: Modified-site
        ( B ) LOCATION: 13
        ( D ) OTHER INFORMATION: 5-fluoro-2'- deoxyuridine substitution ( i x ) FEATURE:
        ( A ) NAME/KEY: Modified-site
        ( B ) LOCATION: 14
        ( D ) OTHER INFORMATION: 5-fluoro-2'- deoxyuridine substitution ( i x ) FEATURE:
        ( A ) NAME/KEY: Modified-site
        ( B ) LOCATION: 15
        ( D ) OTHER INFORMATION: 5-fluoro-2'- deoxyuridine substitution ( x i ) SEQUENCE DESCRIPTION: SEQ ID NO:40:

TCCAGGTGTC CGTTTC 16

( 2 ) INFORMATION FOR SEQ ID NO:41:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: Modified-site
        ( B ) LOCATION: 1
        ( D ) OTHER INFORMATION: 5-fluoro-2'- deoxyuridine
            substitution ( i x ) FEATURE:
        ( A ) NAME/KEY: Modified-site
        ( B ) LOCATION: 7
        ( D ) OTHER INFORMATION: 5-fluoro-2'- deoxyuridine
            substitution ( i x ) FEATURE:
        ( A ) NAME/KEY: Modified-site
        ( B ) LOCATION: 9
        ( D ) OTHER INFORMATION: 5-fluoro-2'- deoxyuridine
            substitution ( i x ) FEATURE:
        ( A ) NAME/KEY: Modified-site
        ( B ) LOCATION: 15
        ( D ) OTHER INFORMATION: 5-fluoro-2'- deoxyuridine
            substitution ( x i ) SEQUENCE DESCRIPTION: SEQ ID NO:41:

TCCAGGTGTC CGCATC 16

( 2 ) INFORMATION FOR SEQ ID NO:42:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: Modified-site
        ( B ) LOCATION: 1
        ( D ) OTHER INFORMATION: 5-bromo-2'- deoxyuridine
            substitution ( i x ) FEATURE:
        ( A ) NAME/KEY: Modified-site
        ( B ) LOCATION: 2
        ( D ) OTHER INFORMATION: 5-bromo-2'- deoxyuridine
            substitution ( i x ) FEATURE:
        ( A ) NAME/KEY: Modified-site
        ( B ) LOCATION: 3
        ( D ) OTHER INFORMATION: 5-bromo-2'- deoxyuridine
            substitution ( i x ) FEATURE:
        ( A ) NAME/KEY: Modified-site
        ( B ) LOCATION: 4
        ( D ) OTHER INFORMATION: 5-bromo-2'- deoxyuridine
            substitution ( i x ) FEATURE:
        ( A ) NAME/KEY: Modified-site ( B ) LOCATION: 5
( D ) OTHER INFORMATION: 5-bromo-2'-deoxyuridine
 substitution ( i x ) FEATURE:
( A ) NAME/KEY: Modified-site
( B ) LOCATION: 6
( D ) OTHER INFORMATION: 5-bromo-2'-deoxyuridine
 substitution ( i x ) FEATURE:
( A ) NAME/KEY: Modified-site
( B ) LOCATION: 7
( D ) OTHER INFORMATION: 5-bromo-2'-deoxyuridine
 substitution ( i x ) FEATURE:
( A ) NAME/KEY: Modified-site
( B ) LOCATION: 8
( D ) OTHER INFORMATION: 5-bromo-2'-deoxyuridine
 substitution ( i x ) FEATURE:
( A ) NAME/KEY: Modified-site
( B ) LOCATION: 9
( D ) OTHER INFORMATION: 5-bromo-2'-deoxyuridine
 substitution ( i x ) FEATURE:
( A ) NAME/KEY: Modified-site
( B ) LOCATION: 10
( D ) OTHER INFORMATION: 5-bromo-2'-deoxyuridine
 substitution ( i x ) FEATURE:
( A ) NAME/KEY: Modified-site
( B ) LOCATION: 11
( D ) OTHER INFORMATION: 5-bromo-2'-deoxyuridine
 substitution ( i x ) FEATURE:
( A ) NAME/KEY: Modified-site
( B ) LOCATION: 12
( D ) OTHER INFORMATION: 5-bromo-2'-deoxyuridine
 substitution ( i x ) FEATURE:
( A ) NAME/KEY: Modified-site
( B ) LOCATION: 13
( D ) OTHER INFORMATION: 5-bromo-2'-deoxyuridine
 substitution ( i x ) FEATURE:
( A ) NAME/KEY: Modified-site
( B ) LOCATION: 14
( D ) OTHER INFORMATION: 5-bromo-2'-deoxyuridine
 substitution ( i x ) FEATURE:
( A ) NAME/KEY: Modified-site
( B ) LOCATION: 15
( D ) OTHER INFORMATION: 5-bromo-2'-deoxyuridine
 substitution ( x i ) SEQUENCE DESCRIPTION: SEQ ID NO:42:

TTTTTTTTT TTTTT       16

( 2 ) INFORMATION FOR SEQ ID NO:43:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:

( A ) NAME/KEY: Modified-site
            ( B ) LOCATION: 15
            ( D ) OTHER INFORMATION: 5-bromo-2'- deoxyuridine
                substitution ( x i ) SEQUENCE DESCRIPTION: SEQ ID NO:43:

TCCAGGTGTC CGCATC                                                                    16

( 2 ) INFORMATION FOR SEQ ID NO:44:

( i ) SEQUENCE CHARACTERISTICS:
            ( A ) LENGTH: 16 base pairs
            ( B ) TYPE: nucleic acid
            ( C ) STRANDEDNESS: single
            ( D ) TOPOLOGY: linear ( i i ) MOLECULE TYPE: DNA (genomic)

( i x ) FEATURE:
            ( A ) NAME/KEY: Modified-site
            ( B ) LOCATION: 1
            ( D ) OTHER INFORMATION: 5-bromo-2'- deoxyuridine
                substitution ( x i ) SEQUENCE DESCRIPTION: SEQ ID NO:44:

TCCAGGTGTC CGCATC                                                                    16

( 2 ) INFORMATION FOR SEQ ID NO:45:

( i ) SEQUENCE CHARACTERISTICS:
            ( A ) LENGTH: 16 base pairs
            ( B ) TYPE: nucleic acid
            ( C ) STRANDEDNESS: single
            ( D ) TOPOLOGY: linear ( i i ) MOLECULE TYPE: DNA (genomic)

( i x ) FEATURE:
            ( A ) NAME/KEY: Modified-site
            ( B ) LOCATION: 7
            ( D ) OTHER INFORMATION: 5-bromo-2'- deoxyuridine
                substitution ( i x ) FEATURE:
            ( A ) NAME/KEY: Modified-site
            ( B ) LOCATION: 9
            ( D ) OTHER INFORMATION: 5-bromo-2'- deoxyuridine
                substitution ( x i ) SEQUENCE DESCRIPTION: SEQ ID NO:45:

TCCAGGTGTC CGCATC                                                                    16

( 2 ) INFORMATION FOR SEQ ID NO:46:

( i ) SEQUENCE CHARACTERISTICS:
            ( A ) LENGTH: 16 base pairs
            ( B ) TYPE: nucleic acid
            ( C ) STRANDEDNESS: single
            ( D ) TOPOLOGY: linear ( i i ) MOLECULE TYPE: DNA (genomic)

( i x ) FEATURE:
            ( A ) NAME/KEY: Modified-site
            ( B ) LOCATION: 13
            ( D ) OTHER INFORMATION: 5-bromo-2'- deoxyuridine
                substitution ( i x ) FEATURE:
            ( A ) NAME/KEY: Modified-site
            ( B ) LOCATION: 14
            ( D ) OTHER INFORMATION: 5-bromo-2'- deoxyuridine
                substitution ( i x ) FEATURE:
    ( A ) NAME/KEY: Modified-site
    ( B ) LOCATION: 15
    ( D ) OTHER INFORMATION: 5-bromo-2'-deoxyuridine
        substitution ( x i ) SEQUENCE DESCRIPTION: SEQ ID NO:46:

TCCAGGTGTC CGTTTC    16

( 2 ) INFORMATION FOR SEQ ID NO:47:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: Modified-site
        ( B ) LOCATION: 1
        ( D ) OTHER INFORMATION: 5-bromo-2'-deoxyuridine
            substitution ( i x ) FEATURE:
        ( A ) NAME/KEY: Modified-site
        ( B ) LOCATION: 7
        ( D ) OTHER INFORMATION: 5-bromo-2'-deoxyuridine
            substitution ( i x ) FEATURE:
        ( A ) NAME/KEY: Modified-site
        ( B ) LOCATION: 9
        ( D ) OTHER INFORMATION: 5-bromo-2'-deoxyuridine
            substitution ( i x ) FEATURE:
        ( A ) NAME/KEY: Modified-site
        ( B ) LOCATION: 15
        ( D ) OTHER INFORMATION: 5-bromo-2'-deoxyuridine
            substitution ( x i ) SEQUENCE DESCRIPTION: SEQ ID NO:47:

TCCAGGTGTC CGCATC    16

( 2 ) INFORMATION FOR SEQ ID NO:48:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: Modified-site
        ( B ) LOCATION: 1
        ( D ) OTHER INFORMATION: 5-bromo-2'-deoxycytidine
            substitution ( i x ) FEATURE:
        ( A ) NAME/KEY: Modified-site
        ( B ) LOCATION: 2
        ( D ) OTHER INFORMATION: 5-bromo-2'-deoxycytidine
            substitution ( i x ) FEATURE:
        ( A ) NAME/KEY: Modified-site
        ( B ) LOCATION: 3
        ( D ) OTHER INFORMATION: 5-bromo-2'-deoxycytidine
            substitution ( i x ) FEATURE:
        ( A ) NAME/KEY: Modified-site ( B ) LOCATION: 4
                    ( D ) OTHER INFORMATION: 5-bromo-2'- deoxycytidine
                        substitution ( i x ) FEATURE:
                    ( A ) NAME/KEY: Modified-site
                    ( B ) LOCATION: 5
                    ( D ) OTHER INFORMATION: 5-bromo-2'- deoxycytidine
                        substitution ( i x ) FEATURE:
                    ( A ) NAME/KEY: Modified-site
                    ( B ) LOCATION: 6
                    ( D ) OTHER INFORMATION: 5-bromo-2'- deoxycytidine
                        substitution ( i x ) FEATURE:
                    ( A ) NAME/KEY: Modified-site
                    ( B ) LOCATION: 7
                    ( D ) OTHER INFORMATION: 5-bromo-2'- deoxycytidine
                        substitution ( i x ) FEATURE:
                    ( A ) NAME/KEY: Modified-site
                    ( B ) LOCATION: 8
                    ( D ) OTHER INFORMATION: 5-bromo-2'- deoxycytidine
                        substitution ( i x ) FEATURE:
                    ( A ) NAME/KEY: Modified-site
                    ( B ) LOCATION: 9
                    ( D ) OTHER INFORMATION: 5-bromo-2'- deoxycytidine
                        substitution ( i x ) FEATURE:
                    ( A ) NAME/KEY: Modified-site
                    ( B ) LOCATION: 10
                    ( D ) OTHER INFORMATION: 5-bromo-2'- deoxycytidine
                        substitution ( i x ) FEATURE:
                    ( A ) NAME/KEY: Modified-site
                    ( B ) LOCATION: 11
                    ( D ) OTHER INFORMATION: 5-bromo-2'- deoxycytidine
                        substitution ( i x ) FEATURE:
                    ( A ) NAME/KEY: Modified-site
                    ( B ) LOCATION: 12
                    ( D ) OTHER INFORMATION: 5-bromo-2'- deoxycytidine
                        substitution ( i x ) FEATURE:
                    ( A ) NAME/KEY: Modified-site
                    ( B ) LOCATION: 13
                    ( D ) OTHER INFORMATION: 5-bromo-2'- deoxycytidine
                        substitution ( i x ) FEATURE:
                    ( A ) NAME/KEY: Modified-site
                    ( B ) LOCATION: 14
                    ( D ) OTHER INFORMATION: 5-bromo-2'- deoxycytidine
                        substitution ( i x ) FEATURE:
                    ( A ) NAME/KEY: Modified-site
                    ( B ) LOCATION: 15
                    ( D ) OTHER INFORMATION: 5-bromo-2'- deoxycytidine
                        substitution ( x i ) SEQUENCE DESCRIPTION: SEQ ID NO:48:

CCCCCCCCCC CCCCCC                                                                                                    1 6

( 2 ) INFORMATION FOR SEQ ID NO:49:

( i ) SEQUENCE CHARACTERISTICS:
                    ( A ) LENGTH: 16 base pairs
                    ( B ) TYPE: nucleic acid ( C ) STRANDEDNESS: single
( D ) TOPOLOGY: linear ( i i ) MOLECULE TYPE: DNA (genomic)

( i x ) FEATURE:
( A ) NAME/KEY: Modified-site
( B ) LOCATION: 1
( D ) OTHER INFORMATION: 5-bromo-2'- deoxycytidine
substitution ( x i ) SEQUENCE DESCRIPTION: SEQ ID NO:49:

CCCAGGTGTC CGCATC    16

( 2 ) INFORMATION FOR SEQ ID NO:50:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: Modified-site
( B ) LOCATION: 15
( D ) OTHER INFORMATION: 5-bromo-2'- deoxycytidine
substitution ( x i ) SEQUENCE DESCRIPTION: SEQ ID NO:50:

TCCAGGTGTC CGCACC    16

( 2 ) INFORMATION FOR SEQ ID NO:51:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: Modified-site
( B ) LOCATION: 10
( D ) OTHER INFORMATION: 5-bromo-2'- deoxycytidine
substitution ( i x ) FEATURE:
( A ) NAME/KEY: Modified-site
( B ) LOCATION: 11
( D ) OTHER INFORMATION: 5-bromo-2'- deoxycytidine
substitution ( x i ) SEQUENCE DESCRIPTION: SEQ ID NO:51:

TCCAGGTGTC CGCATC    16

( 2 ) INFORMATION FOR SEQ ID NO:52:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: Modified-site
( B ) LOCATION: 13
( D ) OTHER INFORMATION: 5-bromo-2'- deoxycytidine
substitution ( i x ) FEATURE:
    ( A ) NAME/KEY: Modified-site
    ( B ) LOCATION: 14
    ( D ) OTHER INFORMATION: 5-bromo-2'- deoxycytidine
          substitution ( i x ) FEATURE:
    ( A ) NAME/KEY: Modified-site
    ( B ) LOCATION: 15
    ( D ) OTHER INFORMATION: 5-bromo-2'- deoxycytidine
          substitution ( x i ) SEQUENCE DESCRIPTION: SEQ ID NO:52:

TCCAGGTGTC CGCCCC    16

( 2 ) INFORMATION FOR SEQ ID NO:53:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: Modified-site
        ( B ) LOCATION: 2
        ( D ) OTHER INFORMATION: 5-bromo-2'- deoxycytidine
              substitution ( i x ) FEATURE:
        ( A ) NAME/KEY: Modified-site
        ( B ) LOCATION: 3
        ( D ) OTHER INFORMATION: 5-bromo-2'- deoxycytidine
              substitution ( i x ) FEATURE:
        ( A ) NAME/KEY: Modified-site
        ( B ) LOCATION: 10
        ( D ) OTHER INFORMATION: 5-bromo-2'- deoxycytidine
              substitution ( i x ) FEATURE:
        ( A ) NAME/KEY: Modified-site
        ( B ) LOCATION: 11
        ( D ) OTHER INFORMATION: 5-bromo-2'- deoxycytidine
              substitution ( i x ) FEATURE:
        ( A ) NAME/KEY: Modified-site
        ( B ) LOCATION: 13
        ( D ) OTHER INFORMATION: 5-bromo-2'- deoxycytidine
              substitution ( x i ) SEQUENCE DESCRIPTION: SEQ ID NO:53:

TCCAGGTGTC CGCATC    16

( 2 ) INFORMATION FOR SEQ ID NO:54:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: Modified-site
        ( B ) LOCATION: 1
        ( D ) OTHER INFORMATION: 5-methyl-2'- deoxycytidine
              substitution ( i x ) FEATURE:
        ( A ) NAME/KEY: Modified-site (B) LOCATION: 2
(D) OTHER INFORMATION: 5-methyl-2'-deoxycytidine
    substitution (ix) FEATURE:
    (A) NAME/KEY: Modified-site
    (B) LOCATION: 3
    (D) OTHER INFORMATION: 5-methyl-2'-deoxycytidine
        substitution (ix) FEATURE:
    (A) NAME/KEY: Modified-site
    (B) LOCATION: 4
    (D) OTHER INFORMATION: 5-methyl-2'-deoxycytidine
        substitution (ix) FEATURE:
    (A) NAME/KEY: Modified-site
    (B) LOCATION: 5
    (D) OTHER INFORMATION: 5-methyl-2'-deoxycytidine
        substitution (ix) FEATURE:
    (A) NAME/KEY: Modified-site
    (B) LOCATION: 6
    (D) OTHER INFORMATION: 5-methyl-2'-deoxycytidine
        substitution (ix) FEATURE:
    (A) NAME/KEY: Modified-site
    (B) LOCATION: 7
    (D) OTHER INFORMATION: 5-methyl-2'-deoxycytidine
        substitution (ix) FEATURE:
    (A) NAME/KEY: Modified-site
    (B) LOCATION: 8
    (D) OTHER INFORMATION: 5-methyl-2'-deoxycytidine
        substitution (ix) FEATURE:
    (A) NAME/KEY: Modified-site
    (B) LOCATION: 9
    (D) OTHER INFORMATION: 5-methyl-2'-deoxycytidine
        substitution (ix) FEATURE:
    (A) NAME/KEY: Modified-site
    (B) LOCATION: 10
    (D) OTHER INFORMATION: 5-methyl-2'-deoxycytidine
        substitution (ix) FEATURE:
    (A) NAME/KEY: Modified-site
    (B) LOCATION: 11
    (D) OTHER INFORMATION: 5-methyl-2'-deoxycytidine
        substitution (ix) FEATURE:
    (A) NAME/KEY: Modified-site
    (B) LOCATION: 12
    (D) OTHER INFORMATION: 5-methyl-2'-deoxycytidine
        substitution (ix) FEATURE:
    (A) NAME/KEY: Modified-site
    (B) LOCATION: 13
    (D) OTHER INFORMATION: 5-methyl-2'-deoxycytidine
        substitution (ix) FEATURE:
    (A) NAME/KEY: Modified-site
    (B) LOCATION: 14
    (D) OTHER INFORMATION: 5-methyl-2'-deoxycytidine
        substitution (ix) FEATURE:
    (A) NAME/KEY: Modified-site
    (B) LOCATION: 15
    (D) OTHER INFORMATION: 5-methyl-2'-deoxycytidine substitution ( x i ) SEQUENCE DESCRIPTION: SEQ ID NO:54:

CCCCCCCCC CCCCC 16

( 2 ) INFORMATION FOR SEQ ID NO:55:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: Modified-site
        ( B ) LOCATION: 1
        ( D ) OTHER INFORMATION: 5-methyl-2'- deoxycytidine
            substitution ( x i ) SEQUENCE DESCRIPTION: SEQ ID NO:55:

CCCAGGTGTC CGCATC 16

( 2 ) INFORMATION FOR SEQ ID NO:56:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: Modified-site
        ( B ) LOCATION: 15
        ( D ) OTHER INFORMATION: 5-methyl-2'- deoxycytidine
            substitution ( x i ) SEQUENCE DESCRIPTION: SEQ ID NO:56:

TCCAGGTGTC CGCACC 16

( 2 ) INFORMATION FOR SEQ ID NO:57:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: Modified-site
        ( B ) LOCATION: 10
        ( D ) OTHER INFORMATION: 5-methyl-2'- deoxycytidine
            substitution ( i x ) FEATURE:
        ( A ) NAME/KEY: Modified-site
        ( B ) LOCATION: 11
        ( D ) OTHER INFORMATION: 5-methyl-2'- deoxycytidine
            substitution ( x i ) SEQUENCE DESCRIPTION: SEQ ID NO:57:

TCCAGGTGTC CGCATC 16

( 2 ) INFORMATION FOR SEQ ID NO:58:

( i ) SEQUENCE CHARACTERISTICS:
        ( A ) LENGTH: 16 base pairs ( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: Modified-site
( B ) LOCATION: 13
( D ) OTHER INFORMATION: 5-methyl-2'- deoxycytidine substitution ( i x ) FEATURE:
( A ) NAME/KEY: Modified-site
( B ) LOCATION: 14
( D ) OTHER INFORMATION: 5-methyl-2'- deoxycytidine substitution ( i x ) FEATURE:
( A ) NAME/KEY: Modified-site
( B ) LOCATION: 15
( D ) OTHER INFORMATION: 5-methyl-2'- deoxycytidine substitution ( x i ) SEQUENCE DESCRIPTION: SEQ ID NO:58:

TCCAGGTGTC CGCCCC    16

( 2 ) INFORMATION FOR SEQ ID NO:59:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: Modified-site
( B ) LOCATION: 2
( D ) OTHER INFORMATION: 5-methyl-2'- deoxycytidine substitution ( i x ) FEATURE:
( A ) NAME/KEY: Modified-site
( B ) LOCATION: 3
( D ) OTHER INFORMATION: 5-methyl-2'- deoxycytidine substitution ( i x ) FEATURE:
( A ) NAME/KEY: Modified-site
( B ) LOCATION: 10
( D ) OTHER INFORMATION: 5-methyl-2'- deoxycytidine substitution ( i x ) FEATURE:
( A ) NAME/KEY: Modified-site
( B ) LOCATION: 11
( D ) OTHER INFORMATION: 5-methyl-2'- deoxycytidine substitution ( i x ) FEATURE:
( A ) NAME/KEY: Modified-site
( B ) LOCATION: 13
( D ) OTHER INFORMATION: 5-methyl-2'- deoxycytidine substitution ( x i ) SEQUENCE DESCRIPTION: SEQ ID NO:59:

TCCAGGTGTC CGCATC    16

( 2 ) INFORMATION FOR SEQ ID NO:60:

( i ) SEQUENCE CHARACTERISTICS:
( A ) LENGTH: 16 base pairs
( B ) TYPE: nucleic acid
( C ) STRANDEDNESS: single (D) TOPOLOGY: linear (i i) MOLECULE TYPE: DNA (genomic)

(i x) FEATURE:
    (A) NAME/KEY: Modified-site
    (B) LOCATION: 1
    (D) OTHER INFORMATION: 5-iodo-2'- deoxyuridine
        substitution (i x) FEATURE:
    (A) NAME/KEY: Modified-site
    (B) LOCATION: 2
    (D) OTHER INFORMATION: 5-iodo-2'- deoxyuridine
        substitution (i x) FEATURE:
    (A) NAME/KEY: Modified-site
    (B) LOCATION: 3
    (D) OTHER INFORMATION: 5-iodo-2'- deoxyuridine
        substitution (i x) FEATURE:
    (A) NAME/KEY: Modified-site
    (B) LOCATION: 4
    (D) OTHER INFORMATION: 5-iodo-2'- deoxyuridine
        substitution (i x) FEATURE:
    (A) NAME/KEY: Modified-site
    (B) LOCATION: 5
    (D) OTHER INFORMATION: 5-iodo-2'- deoxyuridine
        substitution (i x) FEATURE:
    (A) NAME/KEY: Modified-site
    (B) LOCATION: 6
    (D) OTHER INFORMATION: 5-iodo-2'- deoxyuridine
        substitution (i x) FEATURE:
    (A) NAME/KEY: Modified-site
    (B) LOCATION: 7
    (D) OTHER INFORMATION: 5-iodo-2'- deoxyuridine
        substitution (i x) FEATURE:
    (A) NAME/KEY: Modified-site
    (B) LOCATION: 8
    (D) OTHER INFORMATION: 5-iodo-2'- deoxyuridine
        substitution (i x) FEATURE:
    (A) NAME/KEY: Modified-site
    (B) LOCATION: 9
    (D) OTHER INFORMATION: 5-iodo-2'- deoxyuridine
        substitution (i x) FEATURE:
    (A) NAME/KEY: Modified-site
    (B) LOCATION: 10
    (D) OTHER INFORMATION: 5-iodo-2'- deoxyuridine
        substitution (i x) FEATURE:
    (A) NAME/KEY: Modified-site
    (B) LOCATION: 11
    (D) OTHER INFORMATION: 5-iodo-2'- deoxyuridine
        substitution (i x) FEATURE:
    (A) NAME/KEY: Modified-site
    (B) LOCATION: 12
    (D) OTHER INFORMATION: 5-iodo-2'- deoxyuridine
        substitution (i x) FEATURE:
    (A) NAME/KEY: Modified-site
    (B) LOCATION: 13
    (D) OTHER INFORMATION: 5-iodo-2'- deoxyuridine substitution ( i x ) FEATURE:
    ( A ) NAME/KEY: Modified-site
    ( B ) LOCATION: 14
    ( D ) OTHER INFORMATION: 5-iodo-2'- deoxyuridine
        substitution ( i x ) FEATURE:
    ( A ) NAME/KEY: Modified-site
    ( B ) LOCATION: 15
    ( D ) OTHER INFORMATION: 5-iodo-2'- deoxyuridine
        substitution ( x i ) SEQUENCE DESCRIPTION: SEQ ID NO:60:

TTTTTTTTT TTTTT                                           16

( 2 ) INFORMATION FOR SEQ ID NO:61:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: Modified-site
    ( B ) LOCATION: 15
    ( D ) OTHER INFORMATION: 5-iodo-2'- deoxyuridine
        substitution ( x i ) SEQUENCE DESCRIPTION: SEQ ID NO:61:

TCCAGGTGTC CGCATC                                       16

( 2 ) INFORMATION FOR SEQ ID NO:62:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: Modified-site
    ( B ) LOCATION: 1
    ( D ) OTHER INFORMATION: 5-iodo-2'- deoxyuridine
        substitution ( x i ) SEQUENCE DESCRIPTION: SEQ ID NO:62:

TCCAGGTGTC CGCATC                                       16

( 2 ) INFORMATION FOR SEQ ID NO:63:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: Modified-site
    ( B ) LOCATION: 7
    ( D ) OTHER INFORMATION: 5-iodo-2'- deoxyuridine
        substitution ( i x ) FEATURE:
    ( A ) NAME/KEY: Modified-site
    ( B ) LOCATION: 9

( D ) OTHER INFORMATION: 5-iodo-2'- deoxyuridine
substitution ( x i ) SEQUENCE DESCRIPTION: SEQ ID NO:63:

TCCAGGTGTC CGCATC                                                                                                                16

( 2 ) INFORMATION FOR SEQ ID NO:64:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: Modified-site
        ( B ) LOCATION: 13
        ( D ) OTHER INFORMATION: 5-iodo-2'- deoxyuridine
            substitution ( i x ) FEATURE:
        ( A ) NAME/KEY: Modified-site
        ( B ) LOCATION: 14
        ( D ) OTHER INFORMATION: 5-iodo-2'- deoxyuridine
            substitution ( i x ) FEATURE:
        ( A ) NAME/KEY: Modified-site
        ( B ) LOCATION: 15
        ( D ) OTHER INFORMATION: 5-iodo-2'- deoxyuridine
            substitution ( x i ) SEQUENCE DESCRIPTION: SEQ ID NO:64:

TCCAGGTGTC CGTTTC                                                                                                                16

( 2 ) INFORMATION FOR SEQ ID NO:65:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: Modified-site
        ( B ) LOCATION: 1
        ( D ) OTHER INFORMATION: 5-iodo-2'- deoxyuridine
            substitution ( i x ) FEATURE:
        ( A ) NAME/KEY: Modified-site
        ( B ) LOCATION: 7
        ( D ) OTHER INFORMATION: 5-iodo-2'- deoxyuridine
            substitution ( i x ) FEATURE:
        ( A ) NAME/KEY: Modified-site
        ( B ) LOCATION: 9
        ( D ) OTHER INFORMATION: 5-iodo-2'- deoxyuridine
            substitution ( i x ) FEATURE:
        ( A ) NAME/KEY: Modified-site
        ( B ) LOCATION: 15
        ( D ) OTHER INFORMATION: 5-iodo-2'- deoxyuridine
            substitution ( x i ) SEQUENCE DESCRIPTION: SEQ ID NO:65:

TCCAGGTGTC CGCATC                                                                                                                16